(12) United States Patent
Bondarenko et al.

(10) Patent No.: US 9,718,799 B2
(45) Date of Patent: Aug. 1, 2017

(54) 3-ARYL-4H-CHROMENE-4-ONES AS ANTINEOPLASTIC AGENTS FOR THE TREATMENT OF CANCER

(71) Applicant: The University of Kentucky Research Foundation, Lexington, KY (US)

(72) Inventors: Svitlana P. Bondarenko, Kyiv (UA); Mykhaylo S. Frasinyuk, Kyiv (UA); Chunming Liu, Lexington, KY (US); David S. Watt, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/149,940

(22) Filed: May 9, 2016

(65) Prior Publication Data

US 2016/0332981 A1    Nov. 17, 2016

Related U.S. Application Data

(60) Provisional application No. 62/159,669, filed on May 11, 2015.

(51) Int. Cl.
| | | |
|---|---|---|
| *C07D 311/30* | (2006.01) |
| *C07D 407/04* | (2006.01) |
| *C07D 493/14* | (2006.01) |
| *C07D 493/04* | (2006.01) |
| *C07D 405/04* | (2006.01) |

(52) U.S. Cl.
CPC .......... *C07D 311/30* (2013.01); *C07D 405/04* (2013.01); *C07D 407/04* (2013.01); *C07D 493/04* (2013.01); *C07D 493/14* (2013.01)

(58) Field of Classification Search
CPC .. C07D 311/30; C07D 493/14; C07D 493/04; C07D 405/04; C07D 407/04
See application file for complete search history.

(56) References Cited

U.S. PATENT DOCUMENTS

2003/0229065 A1    12/2003  Levy et al.
2006/0167037 A1    7/2006   Kelly et al.

FOREIGN PATENT DOCUMENTS

| CN | 101723938 A | * | 6/2010 |
|---|---|---|---|
| CN | 102241657 A | | 11/2011 |
| WO | 00/62765 A2 | | 10/2000 |
| WO | 03/035635 A1 | | 5/2003 |
| WO | 2010/042933 A2 | | 4/2010 |
| WO | 2014/207069 A1 | | 12/2014 |

OTHER PUBLICATIONS

Gavande et al (ChemMedChem, 2011, 6(8), 1340-1346).*
Frasinyuk et al (Organic & Biomolecular Chemistry, 2015, 13(4), 1053-1067; published Nov. 13, 2014).*
Frasinyuk et al (Organic & Biomolecular Chemistry, 2015, 13(4), 1053-1067; published on Nov. 13, 2014); abstract from STN search report.*
Frasinyuk et al., "Aminomethylation of Cytisine by 3-Hetaryl-7-Hydroxychromones," Chemistry of Natural Compounds, vol. 43, No. 3, 2007, pp. 285-290.
Bondarenko et al., "Synthesis of Flavonoid Derivatives of Cytisine, 3, Synthesis of 7-[2-(Cytisin-12-YL)Ethoxy] Isoflavones," Chemistry of Natural Compounds, vol. 48, No. 6, Jan. 2013, pp. 970-973.
Bondarenko et al., "Synthesis of Cytisine Derivatives of Flavonoids, 2, Aminomethylation of 7-Hydroxyisoflavones," Chemistry of Natural Compounds, vol. 47, No. 4, Sep. 2011, pp. 604-607.
International Search Report and Written Opinion issued in Application No. PCT/US2016/031789 dated Sep. 8, 2016.

* cited by examiner

*Primary Examiner* — Sudhakar Katakam
(74) *Attorney, Agent, or Firm* — McDermott Will & Emery LLP

(57) ABSTRACT

Isoflavonoids or pharmaceutically acceptable salts thereof or pharmaceutically acceptable compositions thereof for the treatment of prostate cancer or for the treatment or inhibition of prostate cancer metastasis in a patient in need thereof are disclosed.

13 Claims, No Drawings

3-ARYL-4H-CHROMENE-4-ONES AS ANTINEOPLASTIC AGENTS FOR THE TREATMENT OF CANCER

CROSS-REFERENCE TO RELATED APPLICATION

This application claims the benefit of U.S. Provisional Application No. 62/159,669 filed May 11, 2015 the entire disclosure of which is hereby incorporated by reference herein.

STATEMENT REGARDING FEDERALLY SPONSORED RESEARCH

This invention was made with government support under Contract No. 2P20 RR020171 awarded by The National Institutes of Health. The Government has certain rights in the invention.

TECHNICAL FIELD

The present disclosure is directed to compounds having antineoplastic activity. In particular, the disclosure is directed to 3-aryl-substituted 4H-chromen-4-ones, commonly referred to as isoflavonoids, and use of such compounds to inhibit cancer cell growth, e.g., prostate cancer, a patient in need thereof.

BACKGROUND

Prostate cancer represents a significant health care burden and is the second leading cause of cancer-related mortality in men. See Siegel, R.; Ma, J.; Zou, Z.; Jemal, A. *CA Cancer J. Clin.* 2014, 64, 9. Among the challenges in this area is the problem of recurrent prostate cancer following androgen-deprivation therapy (i.e., castration). Medical castration initially depletes androgens such as testosterone and its reduced form, 5α-dihydrotestosterone. However, the cancer inevitably reoccurs, and a previously unappreciated but sinister backdoor pathway (Fiandalo, M. V.; Wilton, J.; Mohler, J. L. *Int. J. Biol. Sci.* 2014, 10, 596) converts an intermediate in cholesterol metabolism, 17α-hydroprogesterone first to 4-androstene-3,17-dione and then to dihydrotestosterone without passing through testosterone. Accordingly, there is a continuing need to develop therapies to reduce the elevated levels of these androgens as a means to treat recurrent prostate cancer.

SUMMARY OF THE DISCLOSURE

Advantages of the present disclosure include 3-aryl-substituted 4H-chromen-4-ones or pharmaceutically acceptable salts thereof or pharmaceutically acceptable compositions thereof for the treatment of prostate cancer or for the treatment or inhibition of recurrent prostate cancer in a patient in need thereof.

These and other advantages are satisfied, at least in part, by a 3-aryl-4H-chromen-4-one compound having formula (I) or pharmaceutically acceptable salt thereof:

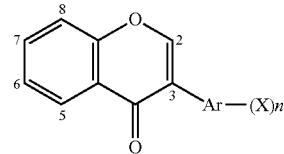

(I)

wherein Ar is an aryl or heteroaryl; n is an integer from 1 to 5; each X is independently a halide, or alkoxy, or more than one X on Ar together form a cyclic ether structure; and wherein the compound is substituted on the C-2 position with H, alkyl, cycloalkyl or alkoxy, substituted on the C-5, C-6, C-7, and C-8 positions independently with H, hydroxy (OH), alkyl, cycloalkyl, alkoxy, or the substituents on either C-6 and C-7 or C-7 and C-8 together form a substituted or unsubstituted, saturated or unsaturated, cyclic or polycyclic ring structure which includes at least one chalcogen, e.g., oxygen or sulfur. The alkyl, cycloalkyl, alkoxy and ring structures can be unsubstituted or substituted. Such substituents include one or more of an amine ($NR^2R^3$), hydroxy, ester, e.g., an acetoxy, alkoxy, carbonyl.

Embodiments include one or more of the following features individually or combined. For example, embodiments of the present disclosure include 3-aryl-4H-chromen-4-ones in which Ar is heteroaryl, such as pyridinyl, diazinyl, pyrimidinyl, oxazolyl or imidazolyl. In some embodiments, Ar is aryl, e.g., phenyl. In other embodiments, the 3-aryl-4H-chromen-4-one has formula (II):

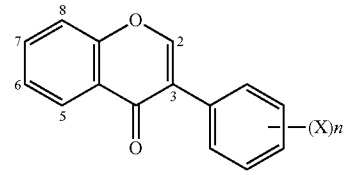

(II)

In various embodiments, the substituents on the 3-aryl-4H-chromen-4-ones (II) include those wherein the C-2 substituent is hydrogen H or methyl; Ar includes one or two X groups on the aryl that can be halogens (e.g., fluorine or chlorine) or alkoxy groups (e.g., methoxy) or together form a ring structure (e.g., methylenedioxy or dimethylenedioxy); the C-5 substituent is hydrogen H, hydroxy (OH) or alkoxy ($OR^1$) where $R^1$ is an alkyl or cycloalkyl group; the C-6 substitutent is hydrogen H; the C-7 substituent is hydroxy or alkoxy ($OR^1$) where $R^1$ is an alkyl or cycloalkyl group; C-8 is hydrogen H, methyl, alkyl or substituted alkyl, such as alkyl-Y where Y represents ($NR^2R^3$), hydroxy, ester, e.g., an acetoxy, alkoxy, where $R^2$ and $R^3$ are independently H, alkyl, e.g., a $C_{1-8}$ alkyl, or C-6 and C-7 together form a ring structure including an oxygen, or C-7 and C-8 together form a ring structure including an oxygen.

Another aspect of the present disclosure includes a pharmaceutical composition of any one or more of the 3-aryl-4H-chromen-4-ones of the present disclosure or one or more pharmaceutically acceptable salts thereof, e.g., one or more compounds of formula (I) and/or formula (II) and/or one or more pharmaceutically acceptable salts of compounds according to formulas (I) and/or (II), in combination with a pharmaceutically acceptable additive, e.g., a pharmaceutically acceptable carrier or excipient. In one aspect of the present disclosure, the pharmaceutical compositions comprise an effective amount of at least one 3-aryl-4H-chromen-4-one or its pharmaceutically acceptable salt.

Another aspect of the present disclosure includes a method of treating prostate cancer. The method comprising administration to a patient in need of such treatment an effective amount of one or more of the 3-aryl-4H-chromen-4-ones of the present disclosure or pharmaceutically acceptable salt thereof or a pharmaceutical composition thereof.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention.

DETAILED DESCRIPTION OF THE DISCLOSURE

The present disclosure relates to 3-aryl-4H-chromen-4-ones that can be used in the treatment of prostate cancer. Considerable lore surrounds the health benefits associated with the consumption of foods rich in natural products in the isoflavone family. In particular, soy products containing 7-hydroxyisoflavones, such as daidzein (A) and genistein (B), captured attention for alleged benefits with respect to cancer prevention and treatment of prostate cancer. See (a) Munro, I. C.; Harwood, M.; Hlywka, J. J.; Stephen, A. M.; Doull, J.; Flamm, W. G.; Adlercreutz, H. *Nutr. Rev.* 2003, 61, 1; (b) Adlercreutz, H. *Scand. J. Clin. Lab. Invest.* 1990, 50, 3; (c) Andres, S.; Abraham, K.; Appel, K. E.; Lampen, *A. Crit. Rev. Toxicol.* 2011, 41, 463. Unfortunately, naturally occurring isoflavones and their metabolites possess numerous biological activities, including effects on androgen receptor expression and enzymes associated with androgen metabolism. Hamilton-Reeves, J. M.; Rebello, S. A.; Thomas, W.; Slaton, J. W.; Kurzer, M. S. *J. Nutr.* 2007, 137, 1769.

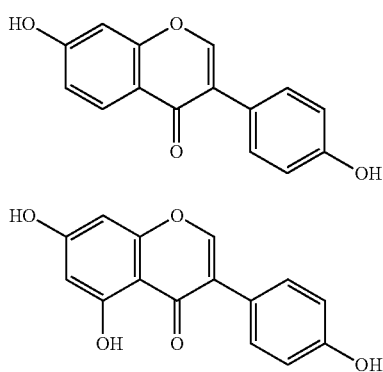

We found that removal of some hydroxyl groups from these natural products and replacement of these groups with functional groups capable of hydrogen bonding and van der Waals interactions led to new agents with unique biological targets.

An advantage of the present disclosure includes 3-aryl-4H-chromen-4-ones or pharmaceutically acceptable salts thereof that can be used for the treatment of prostate cancer or for the treatment or inhibition of recurrent prostate cancer in a patient in need thereof. The 3-aryl-4H-chromen-4-ones of the present disclosure include compounds of formula (I) or pharmaceutically acceptable salt thereof:

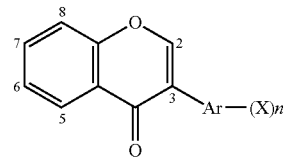

wherein Ar represents aryl, e.g., phenyl, or heteroaryl, e.g., pyridinyl, diazinyl, pyrimidinyl, oxazolyl or imidazolyl. The variable n represents the number of X groups on Ar and can be an integer from 1 to 5. Each X, e.g., $X^1$, $X^2$, $X^3$, $X^4$, and/or $X^5$, is independently a halide, e.g., a fluoro, chloro, or bromo, or alkoxy (—$OR^1$ where $R^1$ is an alkyl or cycloalkyl), or more than one X on Ar together form a cyclic ether structure, e.g., $X^1$ and $X^2$ on Ar together form a —O—R— or —O—R—O— ring, where R is a di-radical organo group. Examples of such groups include a methylenedioxy, dimethylenedioxy, etc. The 3-aryl-4H-chromen-4-one is substituted at each of its C-2, C-5, C-6, C-7, C-8 positions. Each of substituent on these positions can be the same or different and include hydrogen H; hydroxy (OH); alkyl or cycloalkyl; e.g., methyl, ethyl, cyclopropyl; alkoxy; —$COR^1$, e.g., acetyl (—$COCH_3$); ester, etc. In addition, the substituents on either C-6 and C-7 or the substituents on C-7 and C-8 together can form a substituted or unsubstituted, saturated or unsaturated, cyclic or polycyclic ring structure which includes at least one chalcogen, e.g., oxygen or sulfur. In an embodiment of the present disclosure, the compound is substituted on the C-2 position with H, alkyl, or cycloalkyl, substituted on the C-5, C-6, C-7, and C-8 positions independently with H, hydroxy (OH), alkyl or cycloalkyl, alkoxy (—$OR^1$ where $R^1$ is an alkyl or cycloalkyl), or the substituents on C-6 and C-7 or the substituents on C-7 and C-8 together form a substituted or unsubstituted, saturated or unsaturated, cyclic or polycyclic ring structure which includes at least one chalcogen.

The alkyl, cycloalkyl, alkoxy and ring structures described for the various groups and substituents can be unsubstituted or substituted. For example, alkyl, cycloalkyl, alkoxy and ring structures can be substituted with an amine ($NR^2R^3$), hydroxy, ester, e.g., an acetoxy, alkoxy, carbonyl, where $R^2$ and $R^3$ represent independently H, alkyl, e.g., a $C_{1-8}$ alkyl. In some embodiments, C-7 and C-8 independently can be $CH_2OY^1$ where $Y^1$ is hydrogen, alkyl, e.g., methyl, acetyl, etc.

In an embodiment of the present disclosure, the 3-aryl-4H-chromen-4-one is a compound of formula (II) or a pharmaceutically acceptable salt thereof:

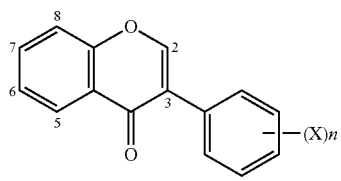

(II)

where C-2, C-5, C-6, C-7, C-8, X and n are as defined above including all embodiments thereof.

The compounds of the present disclosure, including compounds of Formula (I) and Formula (II), can be prepared by methods disclosed herein or any other method known in the art. For example, the regioselective application of the Betti reaction (also called the Mannich reaction) to phenols and β-naphthols provides access to an array of substituted aromatic systems and was adapted in this disclosure for the preparation of substituted 3-aryl-4H-chromen-4-ones. See (a) M. Betti, *Gazz. Chim. Ital.*, 1900, 30, 301-309; (b) M. Betti, *Gazz. Chim. Ital.*, 1900, 30, 310-316; (c) M. Betti, *Gazz. Chim. Ital.*, 1906, 36, 392-394; (d) L. O. Paquette, Ed., *Encyclopedia of Reagents for Organic Synthesis*, 1995, Wiley, UK, 4, 2582. Natural isoflavones, such as genistein (B) from soybeans, were used in clinical trials for prostate cancer prevention and treatment. See Perabo, et al., *Prostate Cancer and Prostate Diseases*, 2008, 11, 6-12.

In the course of developing synthetic 3-aryl-4H-chromen-4-ones as antineoplastic agents, we explored the application of the Betti reaction to isoflavonoids. The rationale for developing these new 3-aryl-4H-chromen-4-ones derives from the low efficacy of naturally occurring isoflavones as antineoplastic agents and the non-specific biological effects of the naturally occurring isoflavones and their metabolites. The $IC_{50}$ of naturally occurring genistein (B) in different cancer cell lines was only ca. 15-100 μM, and the specific biological targets of naturally occurring isoflavones as antineoplastic agents was unclear. In this disclosure, a proliferation assay using a prostate cancer PC3 cell line provided a reasonable surrogate to interrogate structure-activity (SAR) relationships within C-2 substituted and either C-6 or C-8 acetoxymethyl-, hydroxymethyl-, and alkoxymethyl-substituted 3-aryl-7-hydroxy-4H-chromen-4-ones 1 and 2 as well as cyclic counterparts in which there is a substituted or unsubstituted, saturated or unsaturated, cyclic or polycyclic ring structure which includes at least one chalcogen, e.g., oxygen or sulfur, between C-6 and C-7 or between C-7 and C-8 (Scheme 1).

Scheme 1. Biologically active 3-aryl-4H-chromen-4 ones 1 and 2.

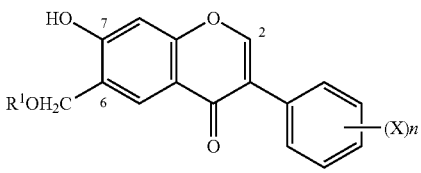

1

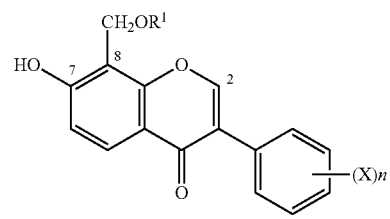

2

A literature report of antineoplastic activity within related natural products included chromones such as 8-(methoxymethyl)eugenin that showed moderate cytotoxicity against P388 leukemia cells. See Y. Feng, J. W. Blunt, A. L. J. Cole and M. H. G. Munro, *J. Nat. Prod.* 2002, 65, 1681-1682. Reports, such as this, are limited because 8-(hydroxymethyl) isoflavonoids are not readily found in nature. As a consequence, this disclosure reveals a general synthetic route to these variously substituted analogs as well as biologically active compounds useful for the treatment of prostate cancer.

Application of the Betti reaction to hydroxylated 3-aryl-4H-chromen-4-ones using bis(N,N-dimethylamino)methane in 1,4-dioxane at 70° C. provided access to dimethylaminomethyl-substituted systems, and their subsequent manipulation furnished the desired acetoxymethyl, hydroxymethyl, and alkoxymethyl derivatives for biological evaluation. See, e.g., Tramontini et al., Mannich Bases-Chemistry and Uses, 1994, CRC Press, Boca Raton, Fla. Synthesis of appropriate starting materials involved the regioselective methylation of the C-7 hydroxy group in 5,7-dihydroxyisoflavonoids to afford 5-hydroxy-2',7-dimethoxyisoflavone (3a) and 4',7-dimethoxygenistein (3b) (Scheme 2) using dimethyl sulfate in the presence of potassium carbonate.

Scheme 2. Betti reaction of 3-aryl-4H-chromen-4-ones or 3-aryl-2-methyl-4H-chromen-4-ones 3.

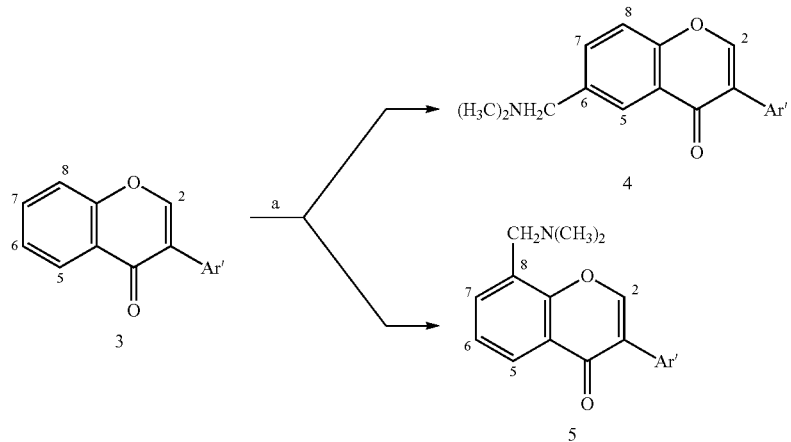

a  C-2 = H, Ar' = C$_6$H$_4$—2—OCH$_3$, C-7 = OCH$_3$, C-5 = OH
b  C-2 = H, Ar' = C$_6$H$_4$—4—OCH$_3$, C-7 = OCH$_3$, C-5 = OH
c  C-2 = H, Ar' = C$_6$H$_4$—2—OCH$_3$, C-7 = OH, C-5 = H
d  C-2 = H, Ar' = C$_6$H$_4$—4—OCH$_3$, C-7 = OH, C-5 = H
e  C-2 = CH$_3$, Ar' = C$_6$H$_4$—4—OCH$_3$, C-7 = OH, C-5 = H
Legend: a, CH$_2$(N(CH$_3$)$_2$)$_2$, DMF, reflux.

In contrast to 5,7-dihydroxy-substituted 3-aryl-4H-chromen-4-ones, which undergo bis-aminomethylation, the 5-hydroxy-substituted 3-aryl-4H-chromen-4-ones 3a and 3b underwent mono-aminomethylation with bis(N,N-dimethylamino)methane in 1,4-dioxane to give a mixture of the 6- and 8-(N,N-dimethylaminomethyl) derivatives 4a-4b and 5a-5b, respectively, (Scheme 2) in which the C-6 isomer predominated. The structures of these isomers were established by HMBC NMR spectroscopy. The 6-(N,N-dimethylamino)methyl derivatives 4a and 4b have cross-peaks for H-2 with C-8a and for H-8 with C-8a. Similar cross-peaks were observed for H-2 with C-8a and for the methylene protons at C-8 with C-8a in compounds 5a and 5b. The aminomethylation of the C-7 hydroxylated 3-aryl-4H-chromen-4-ones 3c-3e with bis(N,N-dimethylamino)methane in isopropanol or 1,4-dioxane gave only the 8-N,N-dimethylamino derivatives 5c-5e. In summary, 5-hydroxylated and 7-hydroxylated 3-aryl-4H-chromen-4-ones underwent the desired aminomethylations using bis(N,N-dimethylamino)methane and exhibited regioselectivity in the C-5 hydroxylated cases in favor of the C-6 (dimethylamino)methyl derivatives 4 and regiospecificity in the C-7 hydroxylated cases in favor of the desired C-8 (dimethylamino)methyl derivatives 5.

Direct conversion of the Betti bases 4 and 5 to the corresponding C-6 or C-8 acetoxymethyl derivatives involved heating the Betti bases 4a-4b or 5a-5e with acetic anhydride in presence of potassium acetate to afford the corresponding diacetates 6 and 7 in excellent yield (Scheme 3).

Scheme 3. Conversion of Betti bases 4 and 5 to acetoxymethyl derivatives 6 and 7, respectively.

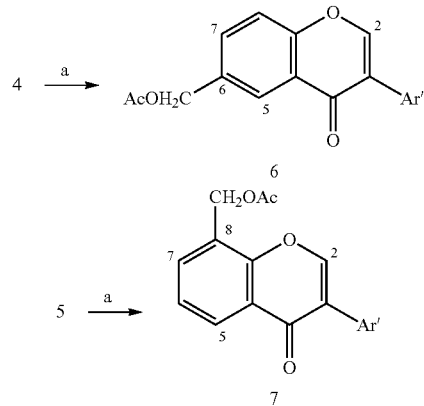

a  C-2 = H, Ar' = C$_6$H$_4$—2—OCH$_3$, C-7 = OCH$_3$, C-5 = OH
b  C-2 = H, Ar' = C$_6$H$_4$—4—OCH$_3$, C-7 = OCH$_3$, C-5 = OH
c  C-2 = H, Ar' = C$_6$H$_4$—2—OCH$_3$, C-7 = OH, C-5 = H
d  C-2 = H, Ar' = C$_6$H$_4$—4—OCH$_3$, C-7 = OH, C-5 = H
e  C-2 = CH$_3$, Ar' = C$_6$H$_4$—4—OCH$_3$, C-7 = OH, C-5 = H
Legend: a, Ac$_2$O, KOAc.

Hydrolysis of the diacetates 6a-6b or 7a-7e using a 2:1 ratio of 0.2M aqueous sulfuric acid in 1,4-dioxane furnished the corresponding hydroxymethyl 3-aryl-4H-chromen-4-ones 8a-8b or 9a-9e, respectively (Scheme 4). Hydrolysis of the diacetates 6 or 7 using hydrochloric acid in methanol led directly to the C-6 or C-8-methoxymethyl 3-aryl-4H-chromen-4-ones 10 and 11, respectively. The substitution of ethanol or isopropanol for methanol led, as expected, to other alkoxymethyl-substituted analogs. Treatment of 8-hydroxymethyl 3-aryl-4H-chromen-4-ones with hydrochloric acid in methanol furnished to the 8-methoxymethyl analogs and treatment of 8-acetoxymethyl derivatives with sodium hydroxide in methanol also led to the 8-methoxymethyl 3-aryl-4H-chromen-4-ones (Scheme 4).

structure in that it retained potency even at 1 mM concentration.

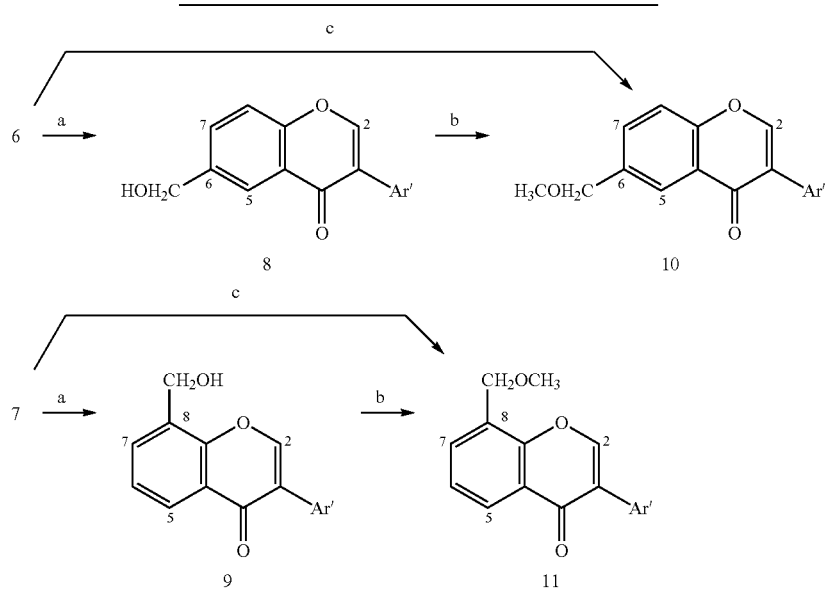

Scheme 4. Conversion of acetoxymethyl derivatives 6 and 7 to hydroxymethyl and methoxymethyl derivatives.

a C-2 = H, Ar' = $C_6H_4$—2—$OCH_3$, C-7 = $OCH_3$, C-5 = OH
b C-2 = H, Ar' = $C_6H_4$—4—$OCH_3$, C-7 = $OCH_3$, C-5 = OH
c C-2 = H, Ar' = $C_6H_4$—2—$OCH_3$, C-7 = OH, C-5 = H
d C-2 = H, Ar' = $C_6H_4$—4—$OCH_3$, C-7 = OH, C-5 = H
e C-2 = $CH_3$, Ar' = $C_6H_4$—4—$OCH_3$, C-7 = OH, C-5 = H
Legend: a, 0.2M $H_2SO_4$, aq. 1,4-dioxane; b, HCl, MeOH; c, NaOH, MeOH.

A screening program using an in vitro PC3 prostate cancer cell line revealed that several 7-hydroxylated 3-aryl-4H-chromen-4-ones 2 with C-8 acetoxymethyl, hydroxymethyl or alkoxymethyl substituents exhibited antineoplastic activity in the 1-10 μM range (Table 1). In general, we observed that C-8 substituted analogs 7, 9 and 11 were more potent at 10 μM concentrations than the C-6 substituted analogs 6, 8 and 10, respectively. Within the C-8 series, the acetoxymethyl- and hydroxymethyl-3-aryl-4H-chromen-4-ones were more potent than the corresponding alkoxymethyl-substituted 3-aryl-4H-chromen-4-ones. Also within the C-8 series, the 3-aryl-4H-chromen-4-ones that possessed a 4-methoxyphenyl group were in general preferable to those with a 2-methoxyphenyl group. For example, 3-aryl-4H-chromen-4-ones 7d and 7e were more potent than 7c; 3-aryl-4H-chromen-4-ones 9b, 9d and 9e were more potent than 9c; and 3-aryl-4H-chromen-4-ones 11b was more potent than 11e. Other substituents than methoxy groups on the 3-phenyl group were also explored and those with halogens were also biologically active. Finally, within the C-8 series, those 3-aryl-4H-chromen-4-ones with 7-hydroxy substituents as well as either 8-acetoxymethyl or 8-hydroxymethyl groups (e.g., 7d and 7e, 9d and 9e) were in general more potent than 3-aryl-4H-chromen-4-ones with 5-hydroxy-7-methoxy groups (e.g., 7b and 9b). The 3-aryl-4H-chromen-4-one 7d with a C-8 acetoxymethyl emerged as a promising lead

TABLE 1

Percent inhibition of proliferation in a prostate cancer PC3 cell assay by isoflavonoids.

| Isoflavonoid | C-6 or C-8 Substituent | Inhibition at 10 μM (%) |
| --- | --- | --- |
| 6a | 6-acetoxymethyl | 17.1 ± 5.9 |
| 6b | 6-acetoxymethyl | 51.7 ± 5.7 |
| 7b | 8-acetoxymethyl | 20.2 ± 2 |
| 7c | 8-acetoxymethyl | 20.6 ± 3.8 |
| 7d | 8-acetoxymethyl | 99.2 ± 0.4 |
| 7e | 8-acetoxymethyl | 98.2 ± 1.5 |
| 8a | 6-hydroxymethyl | 14.6 ± 3.2 |
| 8b | 6-hydroxymethyl | 0 ± 16 |
| 9b | 8-hydroxymethyl | 79.5 ± 3.6 |
| 9c | 8-hydroxymethyl | 0 ± 16 |
| 9d | 8-hydroxymethyl | 99.5 ± 0.2 |
| 9e | 8-hydroxymethyl | 99.5 ± 0.5 |
| 10a | 6-methoxymethyl | 53.4 ± 8 |
| 10b | 6-methoxymethyl | 0 ± 27 |
| 11a | 8-methoxymethyl | 0 ± 1.3 |
| 11b | 8-methoxymethyl | 96.8 ± 0.8 |
| 11c | 8-methoxymethyl | 0 ± 7.4 |
| 11d | 8-methoxymethyl | 34.9 ± 3.3 |

In summary, the Betti reaction of C-5 or C-7 hydroxylated 3-aryl-4H-chromen-4-ones provided N,N-(dimethylamino) methyl derivatives that were readily converted to acetoxymethyl, hydroxymethyl, or alkoxymethyl-substituted 3-aryl-4H-chromen-4-ones. In particular, the 5-hydroxylated 3-aryl-4H-chromen-4-ones 3a-3b afforded C-6 Betti bases 4a-4b regioselectively that led via the diacetates 6a-6b to the C-6 alkoxymethyl derivatives 10a-10b. Analogous reactions of the 7-hydroxylated 3-aryl-4H-chromen-4-ones 3c-3e afforded the C-8 Betti bases 5c-5e regiospecifically, and the diacetates 7c-7e derived from these Mannich bases underwent substitutions leading to the desired C-8 alkoxymethyl derivatives 11c-11e. Several C-8 acetoxymethyl, hydroxymethyl or alkoxymethyl-substituted 3-aryl-4H-chromen-4-ones possessed promising potency in the low micromolar range in a prostate cancer PC3 cell proliferation assay.

In addition to isoflavonoids with various substituents described above, we prepared 3-aryl-4H-chromen-4-ones in which the substituents on C-6 and C-7 or the substituents on C-7 and C-8 together form a substituted or unsubstituted, saturated or unsaturated, cyclic or polycyclic ring structure including at least one oxygen atom. We further show the antineoplastic activity of some of these isoflavonoids.

The generation and Diels-Alder reactions of ortho-quinone methides imbedded within a 3-aryl-4H-chromen-4-ones platform was used to prepare ring-fused analogs of 3-aryl-4H-chromen-4-ones having these cyclic arrangements. In this regard, we synthesized various ring-fused analogs such as the substituted 3-aryl-9,10-dihydropyrano[2,3-*f*]chromen-4(8H)-ones 12 and 3-aryl-10-methyl-3,4-dihydro-2H,6H-pyrano[3,2-g]chromen-6-ones 13 (Scheme 5).

Scheme 5. Representative ring-fused analogs of 3-aryl-4H-chromen-4-ones 12 and 13.

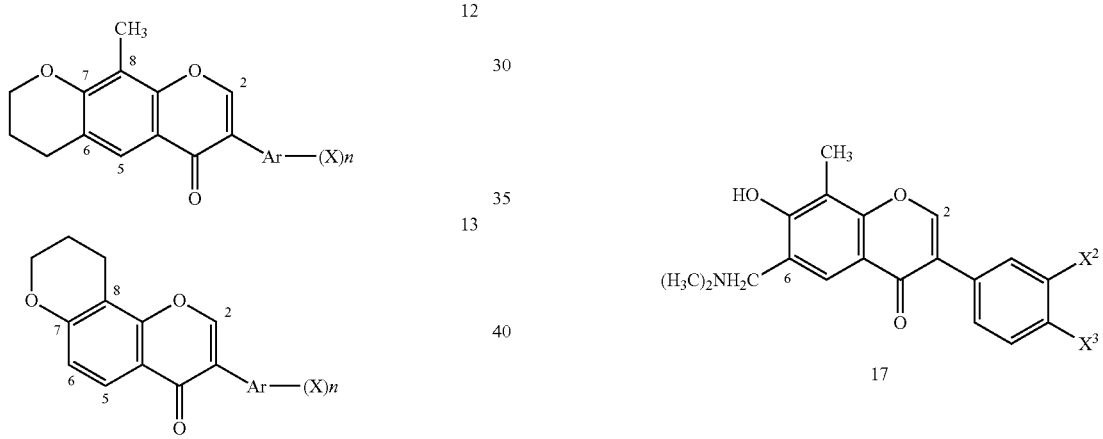

The Betti reaction described earlier in this disclosure provided access to the desired progenitors of ortho-quinone methides that in turn led to ring-fused analogs of 3-aryl-4H-chromen-4-ones. Application of the Betti reaction to 7-hydroxyisoflavonoids 14 with bis(N,N-dimethylamino)methane in isopropanol at reflux provided regioselectively the C-8 substituted N,N-dimethylaminomethyl analogs 15 (Scheme 6) in good yield. The 7-hydroxy-8-methylisoflavonoids 16 gave, as expected, the isomeric C-6 analogs 17.

Scheme 6. Regioselective aminomethylation of 7-hydroxylated 3-aryl-4H-chromen-4-ones 14. and 16

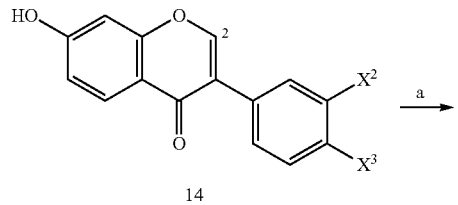

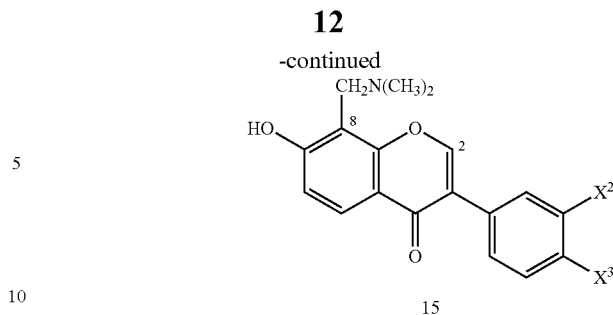

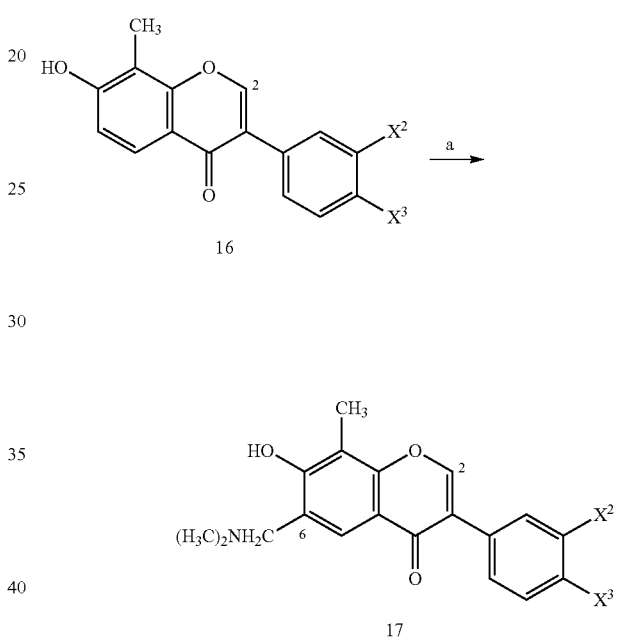

a C-2 = $X^2$ = H, $X^3$ = $OCH_3$
b C-2 = H, $X^2$ = $X^3$ = $OCH_3$
c C-2 = H, $X^2$, $X^3$ = $OCH_2O$
d C-2 = H, $X^2$, $X^3$ = $OCH_2CH_2O$
e C-2 = $X^2$ = H, $X^3$ = Cl
f C-2 = $CH_3$, $X^2$ = $X^3$ = H
g C-2 = $CH_3$, $X^2$ = H, $X^3$ = $OCH_3$
h C-2 = $CH_3$, $X^2$ = $X^3$ = $OCH_3$
i C-2 = $CH_3$, $X^2$ = H, $X^3$ = Cl
Legend: a, $CH_2(N(CH_3)_2)_2$, isopropanol, 80° C.

Heating the N,N-dimethylaminomethyl-substituted isoflavonoids 15 or 17 generated the intermediate ortho-quinone methides 18 and 19, respectively (Scheme 7) that trapped various dienophiles, including 2,3-dihydrofuran, 3,4-dihydro-2H-pyran, 3-(N,N-dimethylamino)-5,5-dimethyl-2-cyclohexen-1-one, 1-morpholinocyclopentene, and 1-morpholinocyclohexene, and led to Diels-Alder adducts 20-26 (Schemes 8 and 9) in yields that varied with dienophile reactivity (Table 2).

Scheme 7. Diels-Alder reactions of N,N-dimethylaminomethyl-substituted 3-aryl-7-hydroxy-4H-chromen-4-ones 15 and 17 with dieneophiles.

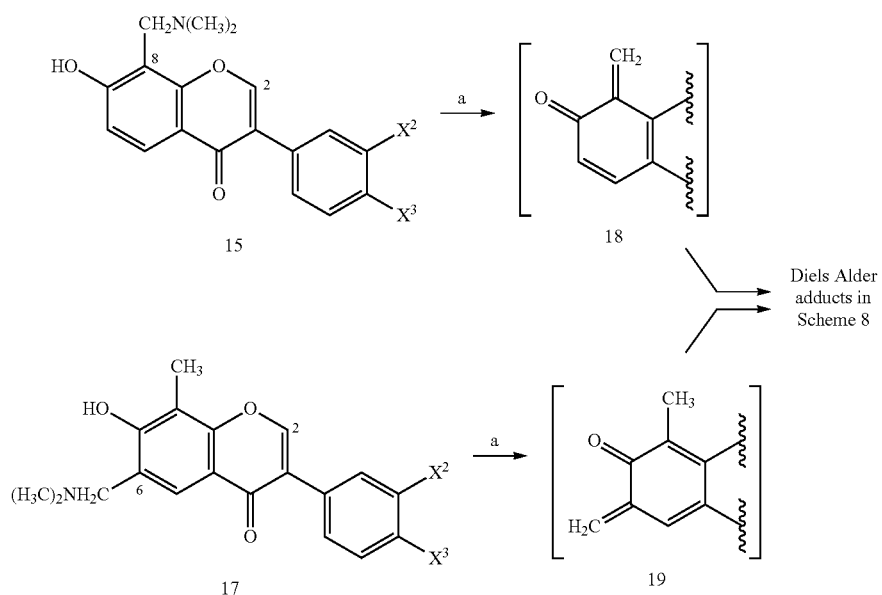

a C-2 = $X^2$ = H, $X^3$ = $OCH_3$
b C-2 = H, $X^2$ = $X^3$ = $OCH_3$
c C-2 = H, $X^2$, $X^3$ = $OCH_2O$
d C-2 = H, $X^2$, $X^3$ = $OCH_2CH_2O$
e C-2 = $X^2$ = H, $X^3$ = Cl
f C-2 = $CH_3$, $X^2$ = $X^3$ = H
g C-2 = $CH_3$, $X^2$ = H, $X^3$ = $OCH_3$
h C-2 = $CH_3$, $X^2$ = $X^3$ = $OCH_3$
i C-2 = $CH_3$, $X^2$ = H, $X^3$ = Cl
Legend: a, dienophiles, DMF, reflux.

The coupling constants $^3J$ between the acetal proton at C-7a and bridgehead proton at C-10a were consistent with the structures of the cis-fused adducts 20 and 21 produced from the C-8 N,N-dimethylaminomethyl-substituted 3-aryl-4H-chromen-4-one 15. The reaction of the isomeric C-6 N,N-dimethylaminomethyl-substituted 3-aryl-4H-chromen-4-ones 17 also led to a cis-fused adduct 16. The Diels-Alder reactions of 15 and 17 with 3-(N,N-dimethylamino)-5,5-dimethyl-2-cyclohexen-1-one led to initial adducts that suffered thermal eliminations of dimethylamine to give the isolated adducts 22 and 26, respectively, in excellent yield. As noted in Table 2, a study of the reaction of 15a with the 3-(N,N-dimethylamino)-5,5-dimethyl-2-cyclohexen-1-one in various solvents led to the selection of refluxing N—N-dimethylformamide as the optimal conditions for these reactions. Finally, Diels-Alder reactions with 1-morpholinocyclopentene and 1-morpholinocyclohexene took a different turn and led to the adducts 23 and 24, respectively. The mechanism leading to these adducts involved either an initial cycloaddition, β-elimination of morpholine, and hydrolysis of the intermediate enol ether or a nucleophilic addition of the enamine to the ortho-quinone methide and subsequent imminium ion hydrolysis. The adduct, in the case of 1-morpholinocyclopentene, adopted the open-chain tautomer 23, and in the case of 1-morpholinocyclohexene, the adduct preferred the cyclic hemiacetal 24. Hydrolysis of either the enol ethers or imminium ions leading to these adducts occurred during isolation and purification.

Scheme 8. Diels-Alder adducts 20-22 derived from thermal reactions of Betti bases 15 or 17 with various dienophiles.

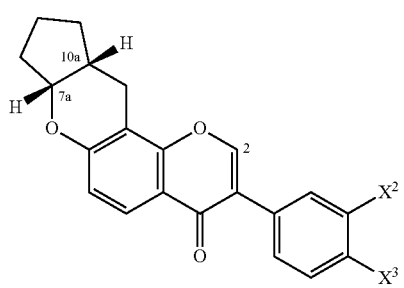

20

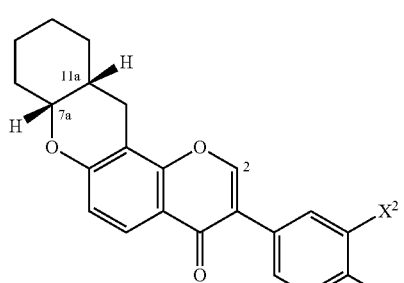

21

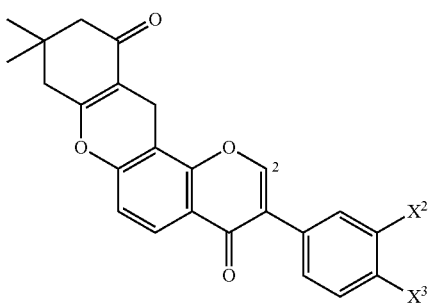

22 a C-2 = X² = H, X³ = OCH₃
b C-2 = H, X² = X³ = OCH₃
c C-2 = H, X², X³ = OCH₂O
d C-2 = H, X², X³ = OCH₂CH₂O
e C-2 = X² = H, X³ = Cl
f C-2 = CH₃, X² = X³ = H
g C-2 = CH₃, X² = H, X³ = OCH₃
h C-2 = CH₃, X² = X³ = OCH₃
i C-2 = CH₃, X² = H, X³ = Cl

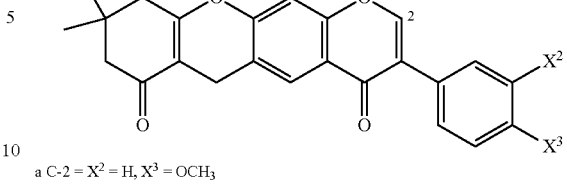

26 a C-2 = X² = H, X³ = OCH₃
b C-2 = H, X² = X³ = OCH₃
c C-2 = H, X², X³ = OCH₂O
d C-2 = H, X², X³ = OCH₂CH₂O
e C-2 = X² = H, X³ = Cl
f C-2 = CH₃, X² = X³ = H
g C-2 = CH₃, X² = H, X³ = OCH₃
h C-2 = CH₃, X² = X³ = OCH₃
i C-2 = CH₃, X² = H, X³ = Cl

Proliferation studies using a prostate cancer PC3 cell line revealed that Diels-Alder adducts formed from 2,3-dihydrofuran or 3,4-dihydro-2H-pyran with the ortho-quinone methide derived from C-8 N,N-dimethylaminomethyl-substituted isoflavonoids 15 produced the most active adducts 20 and 21 (Table 3). In general, adducts 21 were more active than other adducts with a few exceptions. Among the exceptions to this generalization, Adducts 20a and 20e were comparable in activity to 21a and 21e. Similarly, adduct 24g was slightly superior in activity to 21g. With respect to substituents on the isoflavonoid framework, those adducts bearing 3-(4'-methoxyphenyl), 3-(3',4'-dimethoxyphenyl), 3-(3',4'-methylenedioxyphenyl), or 3-(4'-chlorophenyl) substituents were generally the most active. The presence of an additional methyl group at C-2 had relatively little influence on activity with the exception of adduct 24g that was superior in activity to 24a. Most surprising, the adducts generated using 3-(N,N-dimethylamino)-5,5-dimethyl-2-cyclohexen-1-one were generally insoluble with the exception of adduct 22b that displayed 86% inhibition at 10 μM and 31% inhibition at 1 μM.

Scheme 9. More Diels-Alder adducts 23-26 derived from thermal reactions of Betti bases 15 or 17 with various dienophiles.

23

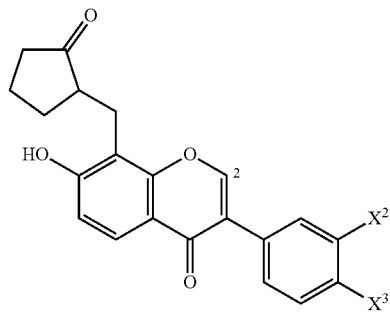

24

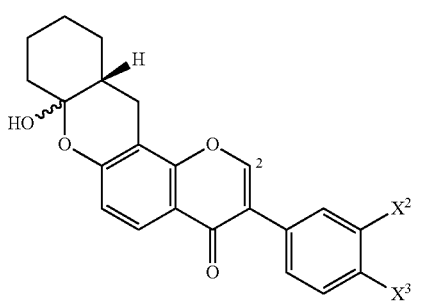

25

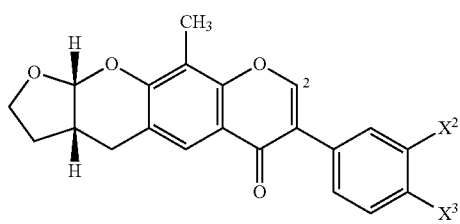

TABLE 2

Isolated yields of Diels-Alder adducts 20-26 from the reaction of dienophiles and ortho-quinone methides derived from 18 and 19.

| Substrate | Dienophile | Solvent, Temperature and Time | Diels-Alder Adduct | Isolated Yield (%) |
|---|---|---|---|---|
| 18a | 2,3-dihydrofuran | DMF, 154° C., 16 h | 20a | 70 |
| 18a | 3,-dihydro-2H-pyran | DMF, 154° C., 16 h | 21a | 30 |
| 18a | 3-(N,N-dimethylamino)-5,5-dimethyl-2-cyclohexen-1-one | 1,4-dioxane, 100° C., 12 h | 22a | 81 |
| 18a | 3-(N,N-dimethylamino)-5,5-dimethyl-2-cyclohexen-1-one | toluene, 110° C. 12 h | 22a | 68 |
| 18a | 3-(N,N-dimethylamino)-5,5-dimethyl-2-cyclohexen-1-one | 2-methoxyethanol, 124° C., 8 h | 22a | 69 |
| 18a | 3-(N,N-dimethylamino)-5,5-dimethyl-2-cyclohexen-1-one | DMSO, 160° C., 4 h | 22a | 71 |
| 18a | 3-(N,N-dimethylamino)-5,5-dimethyl-2-cyclohexen-1-one | DMF, 154° C., 4 h | 22a | 92 |
| 18a | 1-morpholinocyclohexene | DMF, 154° C., 4 h | 24a | 91 |
| 18b | 2,3-dihydrofuran | DMF, 154° C., 16 h | 20b | 29 |
| 18b | 3,-dihydro-2H-pyran | DMF, 154° C., 16 h | 21b | 55 |

TABLE 2-continued

Isolated yields of Diels-Alder adducts 20-26 from the reaction of dienophiles and ortho-quinone methides derived from 18 and 19.

| Substrate | Dienophile | Solvent, Temperature and Time | Diels-Alder Adduct | Isolated Yield (%) |
|---|---|---|---|---|
| 18b | 3-(N,N-dimethylamino)-5,5-dimethyl-2-cyclohexen-1-one | DMF, 154° C., 4 h | 22b | 75 |
| 18b | 1-morpholinocyclohexene | DMF, 154° C., 4 h | 24b | 85 |
| 18c | 2,3-dihydrofuran | DMF, 154° C., 24 h | 20c | 64 |
| 18c | 3,-dihydro-2H-pyran | DMF, 154° C., 24 h | 21c | 25 |
| 18c | 3-(N,N-dimethylamino)-5,5-dimethyl-2-cyclohexen-1-one | DMF, 154° C., 4 h | 22c | 81 |
| 18c | 1-morpholinocyclopentene | DMF, 154° C., 4 h | 24c | 76 |
| 18d | 2,3-dihydrofuran | DMF, 154° C., 24 h | 20d | 75 |
| 18d | 3,-dihydro-2H-pyran | DMF, 154° C., 24 h | 21d | 36 |
| 18e | 2,3-dihydrofuran | DMF, 154° C., 24 h | 20e | 55 |
| 18e | 3,-dihydro-2H-pyran | DMF, 154° C., 24 h | 21e | 19 |
| 18f | 2,3-dihydrofuran | DMF, 154° C., 24 h | 20f | 73 |
| 18f | 3,-dihydro-2H-pyran | DMF, 154° C., 24 h | 21f | 33 |
| 18f | 3-(N,N-dimethylamino)-5,5-dimethyl-2-cyclohexen-1-one | DMF, 154° C., 4 h | 22f | 84 |
| 18g | 2,3-dihydrofuran | DMF, 154° C., 16 h | 20g | 62 |
| 18g | 3,-dihydro-2H-pyran | DMF, 154° C., 4 h | 21g | 34 |
| 18g | 3-(N,N-dimethylamino)-5,5-dimethyl-2-cyclohexen-1-one | DMF, 154° C., 16 h | 22g | 81 |
| 18g | 1-morpholinocyclopentene | DMF, 154° C., 4 h | 23g | 58 |
| 18g | 1-morpholinocyclohexene | DMF, 154° C., 6 h | 24g | 69 |
| 18h | 2,3-dihydrofuran | DMF, 154° C., 24 h | 20h | 56 |
| 18h | 3,-dihydro-2H-pyran | DMF, 154° C., 16 h | 21h | 15 |
| 18h | 1-morpholinocyclopentene | DMF, 154° C., 6 h | 23h | 53 |
| 18h | 1-morpholinocyclohexene | DMF, 154° C., 4 h | 24h | 51 |
| 18i | 2,3-dihydrofuran | DMF, 154° C., 24 h | 20i | 60 |
| 18i | 3,-dihydro-2H-pyran | DMF, 154° C., 24 h | 21i | 15 |
| 18a | 2,3-dihydrofuran | DMF, 154° C., 24 h | 25a | 27 |
| 19a | 3-(N,N-dimethylamino)-5,5-dimethyl-2-cyclohexen-1-one | DMF, 154° C., 4 h | 26a | 81 |
| 19g | 2,3-dihydrofuran | DMF, 154° C., 24 h | 25g | 46 |

TABLE 3

Percent inhibition of proliferation in a prostate cancer PC3 cell assay by Diels-Alder adducts containing 3-aryl-7-hydroxy-4H-chromen-4-one subunits.

| Isoflavonoid Diels-Alder Adduct | Substituents on Isoflavonoid | | Inhibition at 10 μM (%) |
|---|---|---|---|
| | C-2 | C-3 | |
| 20a | H | $C_6H_4$-4-$OCH_3$ | 62 ± 7 |
| 20c | H | $C_6H_3$-3,4-($O_2CH_2$) | 47 ± 4 |
| 20e | H | $C_6H_4$-4-$OCH_3$ | 63 ± 10 |
| 21a | H | $C_6H_4$-4-$OCH_3$ | 73 ± 6 |
| 21b | H | $C_6H_3$-3,4-($OCH_3$)$_2$ | 35 ± 10 |
| 21c | H | $C_6H_3$-3,4-($O_2CH_2$) | 68 ± 0.5 |
| 21d | H | $C_6H_3$-3,4-($O_2[CH_2]_2$) | 48 ± 3 |
| 21e | H | $C_6H_4$-4-Cl | 44 ± 4 |
| 21g | $CH_3$ | $C_6H_4$-4-$OCH_3$ | 62 ± 0.4 |
| 21h | $CH_3$ | $C_6H_3$-3,4-($OCH_3$)$_2$ | 44 ± 3 |
| 21i | $CH_3$ | $C_6H_4$-4-Cl | 74 ± 3 |
| 22b | H | $C_6H_3$-3,4-($OCH_3$)$_2$ | 86 ± 1 |
| 24a | H | $C_6H_4$-4-$OCH_3$ | 30 ± 15 |
| 24b | H | $C_6H_3$-3,4-($OCH_3$)$_2$ | 56 ± 5 |
| 24g | $CH_3$ | $C_6H_4$-4-$OCH_3$ | 78 ± 1 |
| 25a | H | $C_6H_4$-4-$OCH_3$ | 78 ± 3 |
| 25g | $CH_3$ | $C_6H_4$-4-$OCH_3$ | 61 ± 2 |

In summary, a regioselective condensation of 3-aryl-7-hydroxy-4H-chromen-4-ones 14 or 3-aryl-7-hydroxy-8-methyl-4H-chromen-4-ones 16 with bis(N,N-dimethylamino)methane in isopropanol at reflux provided the aminomethylated derivatives 15 or 17, respectively. Thermal eliminations of dimethylamine from these Betti bases 15 and 16 generated ortho-quinone methide intermediates that trapped a variety of dienophiles to give various Diels-Alder adducts 20-26 in generally good yield. These adducts, particularly those derived from 2,3-dihydrofuran, 3,4-dihydro-2H-pyran, or 3-(N,N-dimethylamino)-5,5-dimethyl-2-cyclohexen-1-one, displayed good activity in a proliferation assay using a prostate cancer PC3 cell line.

Another aspect of the present disclosure includes a pharmaceutical composition of any one or more of the 3-aryl-4H-chromen-4-ones of the present disclosure or one or more pharmaceutically acceptable salts thereof, e.g., one or more compounds of formula (I) and/or formula (II) and/or one or more pharmaceutically acceptable salts of compounds according to formulas (I) and/or (II), in combination with a pharmaceutically acceptable additive, e.g., a pharmaceutically acceptable carrier or excipient. In one aspect of the present disclosure, the pharmaceutical compositions comprise an effective amount of at least one 3-aryl-4H-chromen-4-one or its pharmaceutically acceptable salt.

While it may be possible for compounds of the present disclosure to be administered without an additive, it is preferable to present them as a pharmaceutical composition. According to a further aspect, the present disclosure provides a pharmaceutical composition comprising a compound or mixture of compounds of Formula (I) and/or Formula (II) or a pharmaceutically acceptable salt, solvate, or hydrate thereof, together with one or more pharmaceutically acceptable additive, e.g., a pharmaceutically acceptable carrier or excipient and optionally one or more other therapeutic ingredients. The additive(s) must be "acceptable" in the sense of being compatible with the other ingredients of the formulation and not deleterious to the recipient thereof. The term "pharmaceutically acceptable carrier" includes vehicles and diluents.

Another aspect of the present disclosure includes a method of treating prostate cancer. The method comprising administering to a patient in need of such treatment an effective amount of one or more of the 3-aryl-4H-chromen-4-ones, including those with fused rings at C-6 and C-7 or those with fused rings at C-7 and C-8 of the present disclosure or pharmaceutically acceptable salt thereof or a pharmaceutical composition thereof.

Accordingly, the compounds and/or compositions of the present disclosure are useful for treating animals, and in particular, mammals, including humans, as patients. Thus, humans and other animals, and in particular, mammals, suffering from hyperproliferative disorders, and in particular, prostate cancer, can be treated by administering to the patient an effective amount of one or more of the isoflavonoids according to the present disclosure, or its derivative or a pharmaceutically acceptable salt thereof, optionally in a pharmaceutically acceptable additive, either alone, or in combination with other known pharmaceutical agents. Treatment according to the present disclosure can also be by administration of the compounds and/or compositions of the present disclosure in conjunction with other conventional cancer therapies, such as radiation treatment or surgery or administration of other anti-cancer agents.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Characterization: $^1$H and $^{13}$C NMR spectra were recorded on a Varian 500 (500 MHz/125 MHz), Varian 400 (400 MHz/100 MHz) spectrometer in either CDCl$_3$ or DMSO-d$_6$. Structures were also confirmed with HMBC techniques. IR spectra were recorded on a Bruker Vertex 70 FT/IR spectrometer. Melting points were determined using a Buchi B-535 apparatus and were uncorrected. Mass spectra were obtained using an Agilent 1100 spectrometer in chemical ionization mode. Chromatography was performed on Merck silica gel 60.

General Procedure for the Methylation of 3-Aryl-4H-Chromen-4-Ones 3a and 3b.

The procedure of Kim was repeated using 5 mmol of 3, 2.07 g (15 mmol) of anhydrous potassium carbonate and 0.5 mL (5.2 mmol) of dimethyl sulfate in 10 mL of acetone for 6 h to afford the products 3a or 3b. See Kim et al. *Org. Lett.* 2013, 15, 658.

5-Hydroxy-7-methoxy-3-(2-methoxyphenyl)-4H-chromen-4-one (3a)

Pale yellow solid (89% yield); mp 153-154° C.; IR (KBr): $v_{max}$ 2993, 2942, 2839, 1662, 1583, 1495, 1439, 1260, 1181, 748 cm$^{-1}$; $^1$H NMR (400 MHz, DMSO-d$_6$): δ 3.79 (s, 3H, 2'-OCH$_3$). 3.88 (s, 3H, 7-OCH$_3$), 6.33 (s, 1H, 6-H), 6.49 (s, 1H, 8-H), 6.94-7.07 (m, 2H, 3',5'-H), 7.20-7.28 (m, 1H, 6'-H), 7.32-7.41 (m, 1H, 4'-H), 8.06 (s, 1H, 2-H), 12.76 ppm (s, 1H, 5-OH); $^{13}$C NMR (100 MHz, DMSO-d$_6$): δ 55.54, 56.06, 92.50, 98.06, 105.25, 111.29, 119.56, 120.13, 120.73, 129.99, 131.55, 155.59, 157.42, 157.52, 161.59, 165.24, 179.90 ppm; MS (CI): m/z 299.2 (MH$^+$, 100). Anal. Calcd. for C$_{17}$H$_{14}$O$_5$: C, 68.45; H, 4.73. Found: C, 68.12; H, 4.97.

5-Hydroxy-7-methoxy-3-(4-methoxyphenyl)-4H-chromen-4-one (3b)

Pale yellow solid (73% yield); mp 142-143° C.; IR (KBr): $v_{max}$ 2964, 2936, 2833, 1658, 1618, 1579, 1516, 1244, 1192, 1151, 1051 cm$^{-1}$; $^1$H NMR (400 MHz, DMSO-d$_6$): δ 3.79 (s, 3H, 4'-OCH$_3$). 3.86 (s, 3H, 7-OCH$_3$), 6.41 (d, 1H, J=2.2 Hz, 8-H), 6.65 (d, 1H, J=2.2 Hz, 6-H), 7.00 (d, 2H, J=8.8 Hz, 3', 5'-H), 7.51 (d, 2H, J=8.7 Hz, 2',6'-H), 8.44 (s, 1H, 2-H), 12.92 ppm (s, 1H, 5-OH); $^{13}$C NMR (101 MHz, DMSO-d$_6$): δ 55.14, 56.06, 92.40, 98.03, 105.37, 113.68, 122.13, 122.73, 130.11, 154.61, 157.45, 159.17, 161.70, 165.21, 180.25 ppm; MS (CI): m/z 299.1 (MH$^+$, 100). Anal. Calcd. for C$_{17}$H$_{14}$O$_5$: C, 68.45; H, 4.73. Found: C, 68.73; H, 4.94.

General Procedure for the Synthesis of Betti Bases 4a-4b and 5a-5b.

To a suspension of 2 mmol of 3a-3b in 10 mL of 1,4-dioxane was added 1.36 mL (10 mmol) of bis(N,N-dimethylamino)methane. The mixture was refluxed for 24-30 h, cooled and concentrated. The mixture of isomeric Mannich bases 4a-4b and 5a-5b was chromatographed using 1:50 methanol-dichloromethane.

6-[(Dimethylamino)methyl]-5-hydroxy-7-methoxy-3-(2-methoxyphenyl)-4H-chromen-4-one (4a)

Pale yellow solid (48% yield); mp 130-131° C.; IR (KBr): $v_{max}$ 2937, 2809, 2759, 1659, 1585, 1457, 1282, 1222, 1120, 1078 cm$^{-1}$; $^1$H NMR (400 MHz, CDCl$_3$): δ 2.31 (s, 6H, N(CH$_3$)$_2$), 3.52 (s, 2H, 6-CH$_2$), 3.81 (s, 3H, 2'-OCH$_3$), 3.92 (s, 3H, 7-OCH$_3$), 6.43 (s, 1H, 8-H), 6.97-7.06 (m, 2H, 3', 5'-H), 7.28-7.32 (m, 1H, 6'-H), 7.35-7.42 (m, 1H, 4'-H), 7.87 (s, 1H, 2-H), 13.12 ppm (s, 1H, 5-OH); $^{13}$C NMR (101 MHz, CDCl$_3$): δ 45.42, 49.70, 55.71, 56.17, 89.45, 106.06, 109.83, 111.25, 119.66, 120.57, 121.37, 130.05, 131.58, 154.11, 157.37, 157.45, 160.53, 164.22, 180.42 ppm; MS (CI): m/z 356.2 (MH$^+$, 100). Anal. Calcd. for C$_{20}$H$_{21}$NO$_5$: C, 67.59; H, 5.96; N, 3.94. Found: C, 67.87; H, 6.17; N, 4.17.

6-[(Dimethylamino)methyl]-5-hydroxy-7-methoxy-3-(4-methoxyphenyl)-4H-chromen-4-one (4b)

Pale yellow solid (69% yield); mp 140-142° C.; IR (KBr): $v_{max}$ 2933, 2817, 2757, 1653, 1610, 1514, 1254, 1221, 1123, 832 cm$^{-1}$; $^1$H NMR (400 MHz, CDCl$_3$): δ 2.31 (s, 6H, N(CH$_3$)$_2$), 3.53 (s, 2H, 6-CH$_2$), 3.85 (s, 3H, 4'-OCH$_3$), 3.92 (s, 3H, 7-OCH$_3$), 6.42 (s, 1H, 8-H), 6.98 (d, 2H, J=8.8 Hz, 3', 5'-H), 7.46 (d, 2H, J=8.8 Hz, 2', 6'-H), 7.88 (s, 1H, 2-H), 13.10 ppm (s, 1H, 5-OH); $^{13}$C NMR (101 MHz, CDCl$_3$): δ 45.38, 49.65, 55.27, 56.15, 89.41, 105.96, 109.81, 114.00, 122.95, 123.77, 130.04, 152.32, 157.30, 159.67, 160.55, 164.29, 180.69 ppm; MS (CI): m/z 356.3 (MH$^+$, 100). Anal. Calcd. for C$_{20}$H$_{21}$NO$_5$: C, 67.59; H, 5.96; N, 3.94. Found: C, 67.42; H, 6.14; N, 4.23.

8-[(Dimethylamino)methyl]-5-hydroxy-7-methoxy-3-(2-methoxyphenyl)-4H-chromen-4-one (5a)

Pale yellow solid (25% yield); mp 92-93° C.; IR (KBr): $v_{max}$ 2924, 2853, 1654, 1583, 1460, 1312, 1200, 1083, 1017 cm$^{-1}$; $^1$H NMR (400 MHz, CDCl$_3$): δ 2.32 (s, 6H, N(CH$_3$)$_2$), 3.62 (s, 2H, 8-CH$_2$), 3.82 (s, 3H, 2'-OCH$_3$), 3.92 (s, 3H, 7-OCH$_3$), 6.45 (s, 1H, 6-H), 6.98-7.06 (m, 2H, 3', 5'-H), 7.29-7.32 (m, 1H, 6'-H), 7.36-7.42 (m, 1H, 4'-H), 7.94 (s, 1H, 2-H), 13.12 ppm (s, 1H, 5-OH); $^{13}$C NMR (101 MHz): δ 43.66, 49.05, 55.70, 56.45, 95.23, 105.73, 111.21, 119.04, 120.57, 121.19, 130.23, 131.54, 154.62, 156.14, 157.40, 163.89, 164.02, 180.67 ppm; MS (CI): m/z 356.3 (MH$^+$, 100). Anal. Calcd. for C$_{20}$H$_{21}$NO$_5$: C, 67.59; H, 5.96; N, 3.94. Found: C, 67.83; H, 6.21; N, 4.13.

8-[(Dimethylamino)methyl]-5-hydroxy-7-methoxy-3-(4-methoxyphenyl)-4H-chromen-4-one (5b)

Pale yellow solid (28% yield); mp 126-127° C.; IR (KBr): $v_{max}$ 2934, 2832, 1653, 1578, 1513, 1298, 1248, 1200, 1178, 1039 cm$^{-1}$; $^1$H NMR (400 MHz, CDCl$_3$): δ 2.30 (s, 6H, N(CH$_3$)$_2$), 3.58 (s, 2H, 8-CH$_2$), 3.84 (s, 3H, 4'-OCH$_3$), 3.92 (s, 3H, 7-OCH$_3$), 6.44 (s, 1H, 6-H), 6.98 (d, 2H, J=8.8 Hz, 3', 5'-H), 7.46 (d, 2H, J=8.8 Hz, 2', 6'-H), 7.95 (s, 1H, 2-H), 13.13 ppm (s, 1H, 5-OH); $^{13}$C NMR (101 MHz, CDCl$_3$): δ

45.21, 49.78, 55.23, 56.14, 95.06, 104.76, 105.48, 113.96, 122.86, 122.88, 129.97, 152.94, 155.73, 159.62, 162.35, 163.94, 181.16 ppm; MS (CI): m/z 356.3 (MH+, 100). Anal. Calcd. for $C_{20}H_{21}NO_5$: C, 67.59; H, 5.96; N, 3.94. Found: C, 67.65; H, 5.77; N, 3.75.

General Procedure for the Synthesis of Betti Bases 5c-5e.

To a stirred suspension of 2 mmol of 3c-3e in 10 mL of isopropyl alcohol was added 0.3 mL (2.2 mmol) of bis(N, N-dimethylamino)methane. The mixture was heated at 80° C. for 4-6 h and was either cooled to induce crystallization or concentrated and then triturated with hexane to induce crystallization. The compounds were recrystallized from isopropanol-hexane.

8-[(Dimethylamino)methyl]-7-hydroxy-3-(2-methoxyphenyl)-4H-chromen-4-one (5c)

Pale yellow solid (91% yield); mp 120-121° C.; $^1$H NMR (400 MHz, CDCl$_3$): δ 2.43 (s, 6H, N(CH$_3$)$_2$), 3.81 (s, 3H, 2'-OCH$_3$), 3.99 (s, 2H, 8-CH$_2$), 6.89 (d, 1H, $^3$J=8.8 Hz, 6-H), 6.96-7.06 (m, 2H, 3', 5'-H), 7.29-7.40 (m, 2H, 4', 6'-H), 7.88 (s, 1H, H-2), 8.19 (d, 1H, $^3$J=8.8 Hz, 5-H), 12 ppm (br. s, 1H, 7-OH); $^{13}$C NMR (125 MHz, CDCl$_3$): δ 44.41, 54.87, 55.20, 107.27, 113.80, 115.44, 116.89, 124.22, 124.32, 126.67, 130.00, 151.25, 154.96, 159.41, 163.97, 175.74 ppm; IR (KBr): $\nu_{max}$ 3448, 2951, 1626, 1427, 1246, 1178, 1028 cm$^{-1}$; MS (CI): m/z 326.2 (MH$^+$, 100). Anal. Calcd. for $C_{19}H_{19}NO_4$: C, 70.14; H, 5.89; N, 4.30. Found: C, 70.27; H, 5.77; N, 4.17.

8-[Dimethylamino)methyl]-7-hydroxy-3-(4-methoxyphenyl)-4H-chromen-4-one (5d)

Pale yellow solid (83% yield); mp 174-176° C.; IR (KBr): $\nu_{max}$ 3448, 2951, 1626, 1427, 1246, 1178, 1028 cm$^{-1}$; $^1$H NMR (400 MHz, CDCl$_3$): δ 2.44 (s, 6H, N(CH$_3$)$_2$), 3.85 (s, 3H, 4'-OCH$_3$), 3.99 (s, 2H, 8-CH$_2$), 6.90 (d, 1H, $^3$J=8.8 Hz, 6-H), 6.97 (d, 2H, $^3$J=8.8 Hz, 3', 5'-H), 7.50 (d, 2H, $^3$J=8.8 Hz, 2', 6'-H), 7.89 (s, 1H, H-2), 8.14 (d, 1H, $^3$J=8.8 Hz, 5-H), 10.21 ppm (br. s, 1H, 7-OH); $^{13}$C NMR (125 MHz, CDCl$_3$): δ 44.41, 54.87, 55.20, 107.27, 113.80, 115.44, 116.89, 124.22, 124.32, 126.67, 130.00, 151.25, 154.96, 159.41, 163.97, 175.74 ppm; MS (CI): m/z 326.1 (MH$^+$, 100). Anal. Calcd. for $C_{19}H_{19}NO_4$: C, 70.14; H, 5.89; N, 4.30. Found: C, 69.88; H, 5.97; N, 4.39.

8-[(Dimethylamino)methyl]-7-hydroxy-3-(4-methoxyphenyl)-2-methyl-4H-chromen-4-one (5e)

Pale yellow solid (91% yield); mp 185-187° C. (decomp); IR (KBr): $\nu_{max}$ 3450, 2958, 1626, 1603, 1255, 1176, 1016 cm$^{-1}$; $^1$H NMR (400 MHz, CDCl$_3$): δ 2.30 (s, 3H, 2-CH$_3$), 2.44 (s, 6H, N(CH$_3$)$_2$), 3.84 (s, 3H, 4'-OCH$_3$), 3.98 (s, 2H, 8-CH$_2$), 6.85 (d, 1H, $^3$J=8.8 Hz, 6-H), 6.97 (d, 2H, $^3$J=8.7 Hz, 3', 5'-H), 7.20 (d, 2H, $^3$J=8.7 Hz, 2', 6'-H), 8.04 (d, 1H, $^3$J=8.8 Hz, 5-H), 11.30 ppm (br. s, 1H); $^{13}$C NMR (125 MHz, CDCl$_3$): δ 19.28, 44.44, 54.85, 55.21, 106.83, 113.78, 115.03, 115.89, 122.51, 125.33, 126.74, 131.51, 154.68, 158.99, 161.76, 163.69, 176.47 ppm; MS (CI): m/z 340.1 (MH$^+$, 100). Anal. Calcd. for $C_{20}H_{21}NO_4$: C, 70.78; H, 6.24; N, 4.13. Found: C, 70.91; H, 5.95; N, 4.33.

General Procedure for the Synthesis of Diacetates 6a-6b or 7a-7e.

A mixture of Betti base 4a-4b or 5a-5e (2 mmol) and 200 mg (2 mmol) of potassium acetate in 5 mL of acetic anhydride was refluxed for 5 min and cooled to room temperature. The mixture was diluted with water and the precipitate collected and recrystallized from acetonitrile-water.

5-Acetoxy-6-(acetoxymethyl)-7-methoxy-3-(2-methoxyphenyl)-4H-chromen-4-one (6a)

White solid (96% yield); mp 143-145° C.; IR (KBr): $\nu_{max}$ 2945, 2836, 1767, 1738, 1650, 1617, 1451, 1280, 1235, 1127 cm$^{-1}$; $^1$H NMR (400 MHz, CDCl$_3$): δ 2.04 (s, 3H, C-6 CH$_2$OCOC$\underline{H}_3$), 2.41 (s, 3H, C-5 OCOCH$_3$), 3.78 (s, 3H, 2'-OCH$_3$), 3.96 (s, 3H, 7-OCH$_3$), 5.21 (br. s, 2H, 6-CH$_2$), 6.80 (s, 1H, 8-H), 6.93-7.03 (m, 2H, 3', 5'-H), 7.24-7.29 (m, 1H, 6'-H), 7.32-7.38 (m, 1H, 4'-H), 7.80 ppm (s, 1H, 2-H); $^{13}$C NMR (101 MHz, CDCl$_3$): δ 20.85, 21.10, 54.69, 55.68, 56.35, 97.13, 111.34, 111.69, 115.90, 120.52, 120.52, 123.43, 129.85, 131.67, 150.12, 152.45, 157.40, 158.93, 161.92, 169.32, 170.80, 174.02 ppm; MS (CI): m/z 413.2 (MH$^+$, 100). Anal. Calcd. for $C_{22}H_{20}O_8$: C, 64.08; H, 4.89. Found: C, 64.27; H, 5.11.

5-Acetoxy-6-(acetoxymethyl)-7-methoxy-3-(4-methoxyphenyl)-4H-chromen-4-one (6b)

White solid (97% yield); mp 167-169° C.; IR (KBr): $\nu_{max}$ 2962, 2834, 1734, 1629, 1513, 1453, 1248, 1182, 1123 cm$^{-1}$; $^1$H NMR (400 MHz, CDCl$_3$): δ 2.04 (s, 3H, C-6 CH$_2$OCOC$\underline{H}_3$), 2.44 (s, 3H, C-5 OCOCH$_3$), 3.83 (s, 3H, 4'-OCH$_3$), 3.96 (s, 3H, 7-OCH$_3$), 5.20 (s, 2H, 6-CH$_2$), 6.80 (s, 1H, 8-H), 6.94 (d, 2H, J=8.8 Hz, 3', 5'-H), 7.39 (d, 2H, J=8.8 Hz, 2', 6'-H), 7.81 ppm (s, 1H, 2-H); $^{13}$C NMR (101 MHz, CDCl$_3$): δ 20.83, 21.08, 54.62, 55.25, 56.35, 97.06, 111.53, 113.91, 116.01, 123.58, 125.95, 130.25, 150.18, 150.85, 158.88, 159.58, 162.00, 169.38, 170.77, 174.40 ppm; MS (CI): m/z 413.2 (MH$^+$, 100). Anal. Calcd. for $C_{22}H_{20}O_8$: C, 64.08; H, 4.89. Found: C, 63.89; H, 5.17.

[7-(Acetyloxy)-3-(4-methoxyphenyl)-8-methyl-4-oxo-4H-chromen-6-yl]methyl acetate (6c)

White solid (93% yield); mp 136-138° C.; IR (KBr): $\nu_{max}$ 3074, 2839, 1767, 1742, 1642, 1291, 1232, 1176 cm$^{-1}$; $^1$H NMR (400 MHz, CDCl$_3$): δ 2.09 (s, 3H, C-8 CH$_2$OCOC$\underline{H}_3$), 2.30 (s, 3H, 8-CH$_3$), 2.41 (s, 3H, 7-OCOCH$_3$), 2.40 (s, 3H, C-7 OCOCH$_3$), 3.85 (s, 3H, 4'-OCH$_3$) 5.14 (s, 2H, 6-CH$_2$), 6.99 (d, 2H, $^3$J=8.8 Hz, 3', 5'-H), 7.51 (d, 2H, $^3$J=8.8 Hz, 2', 6'-H), 8.04 (s, 1H, H-2), 8.26 ppm (s, 1H, 5-H); $^{13}$C NMR (100 MHz, CDCl$_3$): δ 9.44, 20.49, 20.82, 55.29, 61.28, 113.90, 121.05, 122.21, 123.59, 124.80, 125.08, 126.11, 129.93, 151.10, 152.36, 154.89, 159.54, 168.03, 170.35, 175.75 ppm; MS (CI): m/z 397.2 (MH$^+$, 100). Anal. Calcd. for $C_{21}H_{18}O_7$: C, 66.66; H, 5.09. Found: C, 66.91; H, 4.89.

5-Acetoxy-8-(acetoxymethyl)-7-methoxy-3-(2-methoxyphenyl)-4H-chromen-4-one (7a)

White solid (98% yield); mp 116-118° C.; IR (KBr): $\nu_{max}$ 2946, 1759, 1652, 1537, 1389, 1254, 1157, 1022 cm$^{-1}$; $^1$H NMR (400 MHz, CDCl$_3$): δ 2.09 (s, 3H, C-8 CH$_2$OCOC$\underline{H}_3$), 2.40 (s, 3H, C-5 OCOCH$_3$), 3.79 (s, 3H, 2'-OCH$_3$), 3.96 (s, 3H, 7-OCH$_3$), 5.36 (s, 2H, 8-CH$_2$), 6.67 (s, 1H, 6-H), 6.94-7.10 (m, 2H, 3', 5'-H), 7.24-7.29 (m, 1H, 6'-H), 7.24-7.28 (m, 1H, 4'-H), 7.86 ppm (s, 1H, 2-H); $^{13}$C NMR (101 MHz, CDCl$_3$): δ 20.74, 20.98, 54.38, 55.39, 56.12, 103.49, 109.19, 110.93, 111.38, 119.87, 120.18, 122.50, 129.53, 131.34, 151.37, 152.36, 156.56, 156.99, 161.36, 169.18, 170.72, 173.95 ppm; MS (CI): m/z 413.2 (MH$^+$, 100). Anal. Calcd. for $C_{22}H_{20}O_8$: C, 64.08; H, 4.89. Found: C, 64.32; H, 5.07.

5-Acetoxy-8-(acetoxymethyl)-7-methoxy-3-(4-methoxyphenyl)-4H-chromen-4-one (7b)

White solid (88% yield); mp 124-126° C.; IR (KBr): $\nu_{max}$ 2943, 2840, 1763, 1740, 1645, 1515, 1411, 1304, 1247, 1182, 1026 cm$^{-1}$; $^1$H NMR (400 MHz, CDCl$_3$): δ 2.09 (s, 3H, C-8 CH$_2$OCOC$\underline{H}_3$), 2.44 (s, 3H, C-5 OCOCH$_3$), 3.84 (s, 3H, 4'-OCH$_3$), 3.97 (s, 3H, 7-OCH$_3$), 5.37 (s, 2H, 8-CH$_2$), 6.68 (s, 1H, 6-H), 6.96 (d, 2H, J=8.8 Hz, 3', 5'-H), 7.41 (d, 2H, J=8.8 Hz, 2', 6'-H), 7.87 ppm (s, 1H, 2-H); $^{13}$C NMR (101 MHz, CDCl$_3$): δ 20.95, 21.21, 54.57, 55.28, 56.41, 103.95, 109.54, 111.61, 113.97, 123.49, 125.46, 130.27, 151.07, 151.86, 156.91, 159.63, 161.83, 169.59, 171.02, 174.73 ppm; MS (CI): m/z 413.3 (MH$^+$, 100). Anal. Calcd. for $C_{22}H_{20}O_8$: C, 64.08; H, 4.89. Found: C, 63.85; H, 4.61.

7-(Acetoxy)-8-(acetoxymethyl)-3-(2-methoxyphenyl)-4H-chromen-4-one (7c)

White solid (98% yield); mp 122-124° C.; IR (KBr): $\nu_{max}$ 3076, 1759, 1741, 1660, 1255, 1236 and 1178 cm$^{-1}$; $^1$H NMR (400 MHz, CDCl$_3$): δ 2.08 (s, 3H, C-8 CH$_2$OCOC$\underline{H}_3$), 2.40 (s, 3H, C-7 OCOCH$_3$), 3.82 (s, 3H, 2'-OCH$_3$) 5.40 (s, 2H, 8-CH$_2$), 6.97-7.07 (m, 2H, 3', 5'-H), 7.21 (d, 1H, $^3$J=8.8 Hz, 6-H), 7.30-7.35 (m, 1H, 6'-H), 7.37-7.42 (m, 1H, 4'-H), 8.04 (s, 1H, H-2), 8.35 ppm (d, 1H, $^3$J=8.8 Hz, 5-H); $^{13}$C NMR (125 MHz, CDCl$_3$): δ 20.70, 20.79, 54.46, 55.29, 114.03, 117.52, 120.31, 122.54, 123.47, 125.16, 128.06, 130.03, 152.28, 153.65, 155.38, 159.77, 168.63, 170.52, 175.59 ppm; MS (CI): m/z 383.1 (MH$^+$, 100). Anal. Calcd. for $C_{21}H_{18}O_7$: C, 65.97; H, 4.75. Found: C, 65.83; H, 4.95.

7-(Acetoxy)-8-(acetoxymethyl)-3-(4-methoxyphenyl)-4H-chromen-4-one (7d)

Pale yellow solid (84% yield); mp 141-143° C.; IR (KBr): $\nu_{max}$ 3076, 1759, 1741, 1660, 1255, 1236 and 1178 cm$^{-1}$; $^1$H NMR (400 MHz, CDCl$_3$): δ 2.07 (s, 3H, C-8 CH$_2$OCOC$\underline{H}_3$), 2.40 (s, 3H, C-7 OCOCH$_3$), 3.85 (s, 3H, 4'-OCH$_3$) 5.39 (s, 2H, 8-CH$_2$), 6.99 (d, 2H, $^3$J=8.8 Hz, 3', 5'-H), 7.21 (d, 1H, $^3$J=8.8 Hz, 6-H), 7.51 (d, 2H, $^3$J=8.8 Hz, 2', 6'-H), 8.06 (s, 1H, 2-H), 8.36 ppm (d, 1H, $^3$J=8.8 Hz, 5-H); $^{13}$C NMR (125 MHz, CDCl$_3$): δ 20.69, 20.78, 54.45, 55.29, 114.02, 117.51, 120.30, 122.53, 123.46, 125.15, 128.05, 130.02, 152.27, 153.64, 155.37, 159.77, 168.62, 170.51, 175.59 ppm; MS (CI): m/z 383.1 (MH$^+$, 100). Anal. Calcd. for $C_{21}H_{18}O_7$: C, 65.97; H, 4.75. Found: C, 66.21; H, 4.51.

7-(Acetoxy)-8-(acetoxymethyl)-3-(4-methoxyphenyl)-2-methyl-4H-chromen-4-one (7e)

White crystals (77% yield); mp 142-144° C.; IR (KBr): $\nu_{max}$ 2922, 1765, 1737, 1645, 1223, 1199, 1180 cm$^{-1}$; $^1$H NMR (400 MHz, CDCl$_3$): δ 2.08 (s, 3H, C-8 CH$_2$OCOC$\underline{H}_3$), 2.36 (s, 3H, 2-CH$_3$), 2.39 (s, 3H, C-7 OCOCH$_3$), 3.85 (s, 3H, 4'-OCH$_3$), 5.40 (s, 2H, 8-CH$_2$), 6.98 (d, 2H, $^3$J=8.3 Hz, 3', 5'-H), 7.16 (d, 1H, $^3$J=8.8 Hz, 6-H), 7.21 (d, 2H, $^3$J=8.3 Hz, 2', 6'-H), 8.28 ppm (d, 1H, $^3$J=8.8 Hz, 5-H); $^{13}$C NMR (125 MHz, CDCl$_3$): δ 19.45, 20.72, 20.78, 54.55, 55.24, 113.93, 117.08, 119.84, 121.51, 123.30, 124.57, 127.94, 131.42, 153.46, 154.92, 159.22, 163.21, 168.66, 170.50, 176.11 ppm; MS (CI): m/z 397.2 (MH$^+$, 100). Anal. Calcd. for $C_{22}H_{20}O_7$: C, 66.66; H, 5.09. Found: C, 66.41; H, 5.27.

General Procedures for the Synthesis of Hydroxymethyl Derivatives 8a-8b, 9a-9b and 9d-9e.

To a solution of 6 or 7 (1 mmol) in 10 mL of 1,4-dioxane and 20 mL of 0.2 M aqueous sulfuric acid. The mixture was heated at 50-60° C. for 6-8 h. The mixture was cooled and diluted with water, and the resulting precipitate was collected by filtration. The crude product was chromatographed using 1-20 methanol-dichloromethane and recrystallized from acetonitrile.

5-Hydroxy-6-(hydroxymethyl)-7-methoxy-3-(2-methoxyphenyl)-4H-chromen-4-one (8a)

White solid (25%); mp 100-101° C.; IR (KBr): $\nu_{max}$ 2938, 2837, 1654, 1583, 1494, 1283, 1220, 1129, 1076 cm$^{-1}$; $^1$H NMR (400 MHz, CDCl$_3$): δ 3.81 (s, 3H, 2'-OCH$_3$), 3.93 (s, 3H, 7-OCH$_3$), 4.81 (s, 2H, 6C$\underline{H}_2$OH), 6.43 (s, 1H, 8-H), 6.94-7.08 (m, 2H, 3', 5'-H), 7.27-7.45 (m, 2H, 4', 6'-H), 7.88 (s, 1H, 2-H), 13.19 ppm (s, 1H, 5-OH); $^{13}$C NMR (101 MHz, CDCl$_3$): δ 53.71, 55.70, 56.07, 89.67, 106.18, 111.24 (111.92), 119.37, 120.57, 121.38, 130.15, 131.54, 154.40, 157.40, 157.57, 159.90, 163.20, 180.53 ppm; MS (CI): m/z 329.1 (MH$^+$, 100). Anal. Calcd. for $C_{18}H_{16}O_6$: C, 65.85; H, 4.91. Found: C, 65.93; H, 5.07.

5-Hydroxy-6-(hydroxymethyl)-7-methoxy-3-(4-methoxyphenyl)-4H-chromen-4-one (8b)

White solid (37% yield); mp 138-139° C.; IR (KBr): vhd max 2930, 2833, 1645, 1611, 1513, 1253, 1223, 1179, 836 cm$^{-1}$; $^1$H NMR (400 MHz, CDCl$_3$): δ 3.80 (s, 3H, 4'-OCH$_3$), 3.92 (s, 3H, 7-OCH$_3$), 4.48 (s, 2H, 6-C$\underline{H}_2$OH), 6.74 (s, 1H, 8-H), 6.96-7.05 (m, 2H, 3', 5'-H), 7.47-7.58 (m, 2H, 2', 6'-H), 8.48 (s, 1H, 2-H), 13.23 ppm (s, 1H, 5-OH); $^{13}$C NMR (101 MHz, CDCl$_3$): δ 53.68, 55.31, 56.08, 89.65, 106.12, 111.99, 114.07, 122.73, 123.84, 130.04, 152.57, 157.53, 159.80, 159.98, 163.34, 180.83 ppm; MS (CI): m/z (%): 329.2 (MH$^+$, 100). Anal. Calcd. for $C_{18}H_{16}O_6$: C, 65.85; H, 4.91. Found: C, 65.56; H, 4.87.

7-Hydroxy-6-(hydroxymethyl)-3-(4-methoxyphenyl)-8-methyl-4H-chromen-4-one (8c)

White crystals (72% yield); mp 153-155° C.; IR (KBr): $\nu_{max}$ 2929, 1636, 1580, 1512, 1231, 1174, 1112, 1084 cm$^{-1}$; $^1$H NMR (400 MHz, DMSO-d$_6$): δ 2.29 (s, 3H, 8-CH$_3$), 3.79 (s, 3H, 4'-OCH$_3$), 4.64 (s, 3H, 6-C$\underline{H}_2$OH), 5.45 (s, 3H, 6-CH$_2$O$\underline{H}$), 6.99 (d, 2H, $^3$J=8.7 Hz, 3', 5'-H), 7.52 (d, 2H, $^3$J=8.7 Hz, 2', 6'-H), 7.96 (s, 1H, 5-H), 8.42 (s, 1H, 2-H), 9.73 ppm (s, 1H, 7-OH); $^{13}$C NMR (100 MHz, DMSO-d$_6$): δ 8.44, 55.11, 59.02, 111.01, 113.51, 116.50, 120.73, 122.66, 124.32, 127.94, 129.97, 153.01, 154.21, 156.84, 158.77, 174.92 ppm; MS (CI): m/z 313.3 (MH$^+$, 100). Anal. Calcd. for $C_{18}H_{16}O_5$: C, 69.22; H, 5.16. Found: C, 69.01; H, 5.45.

5-Hydroxy-8-(hydroxymethyl)-7-methoxy-3-(4-methoxyphenyl)-4H-chromen-4-one (9b)

White solid (48% yield); mp 139-141° C.; IR (KBr): $\nu_{max}$ 2938, 2835, 1656, 1610, 1582, 1514, 1250, 1178, 1040, 831 cm$^{-1}$; $^1$H NMR (400 MHz, CDCl$_3$): δ 3.85 (s, 3H, 4'-OCH$_3$), 3.96 (s, 3H, 7-OCH$_3$), 4.86 (s, 2H, 8-C$\underline{H}_2$OH), 6.44 (s, 1H, 6-H), 6.99 (d, 2H, $^3$J=8.8 Hz, 3', 5'-H), 7.46 (d, 2H, $^3$J=8.8 Hz, 2', 6'-H), 7.94 (s, 1H, 2-H), 13.14 ppm (s, 1H, 5-OH); $^{13}$C NMR (101 MHz, CDCl$_3$): δ 56.35, 55.36, 56.25, 95.22, 105.56, 106.97, 114.08, 122.70, 123.29, 130.03, 152.66, 154.91, 159.76, 163.03, 163.56, 181.11 ppm; MS (CI): m/z 329.2 (MH$^+$, 100). Anal. Calcd. for $C_{18}H_{16}O_6$: C, 65.85; H, 4.91. Found: C, 65.68; H, 5.11.

7-Hydroxy-8-(hydroxymethyl)-3-(2-methoxyphenyl)-4H-chromen-4-one (9c)

White crystals (63% yield); mp 163-165° C.; IR (KBr): $\nu_{max}$ 2953, 1627, 1603, 1441, 1267, 1237 cm$^{-1}$; $^1$H NMR (400 MHz, DMSO-d$_6$): δ 3.71 (s, 3H, 2'-OCH$_3$), 4.72 (s, 2H, 8-C$\underline{H}_2$OH), 6.82 (d, 1H, $^3$J=8.8 Hz, 6-H), 6.95-7.02 (m, 1H, 5'-H), 7.04-7.10 (m, 1H, 3'-H), 7.19-7.25 (m, 1H, 6'-H), 7.32-7.39 (m, 1H, 4'-H), 7.75 (d, 1H, $^3$J=8.8 Hz, 5-H), 8.12 ppm (s, 1H, H-2); $^{13}$C NMR (125 MHz, DMSO-d$_6$): δ 51.39, 55.13, 113.60, 114.59, 114.87, 116.60, 122.88, 124.25, 125.91, 130.06, 153.10, 155.85, 158.94, 160.51, 174.86 ppm; MS (CI): m/z (%) 299.2 (MH$^+$, 100). Anal. Calcd. for $C_{17}H_{14}O_5$: C, 68.45; H, 4.73. Found: C, 68.55; H, 4.93.

7-Hydroxy-8-(hydroxymethyl)-3-(4-methoxyphenyl)-4H-chromen-4-one (9d)

White crystals (69% yield); mp 150-152° C. (decomp); IR (KBr): $\nu_{max}$ 2953, 1627, 1603, 1441, 1267, 1237 cm$^{-1}$; $^1$H NMR (400 MHz, DMSO-d$_6$): δ 3.79 (s, 3H, 4'-OCH$_3$), 4.70 (s, 2H, 8-CH$_2$), 4.91 (br s, 1H, 8-CH$_2$O$\underline{H}$), 6.95-7.05 (m, 3H, 6, 3', 5'-H), 7.52 (d, 2H, $^3$J=8.8 Hz, 2', 6'-H), 7.93 (d, 1H, $^3$J=8.8 Hz, 5-H), 8.41 (s, 1H, 2-H), 10.77 ppm (s, 1H, 7-OH); $^{13}$C NMR (125 MHz, DMSO-d$_6$): δ 51.39, 55.13, 113.60, 114.59, 114.87, 116.60, 122.88, 124.25, 125.91, 130.06, 153.10, 155.85, 158.94, 160.51, 174.86 ppm; MS (CI): m/z (%) 299.1 (MH$^+$, 100). Anal. Calcd. for $C_{17}H_{14}O_5$: C, 68.45; H, 4.73. Found: C, 68.72; H, 4.58.

7-Hydroxy-8-(hydroxymethyl)-3-(4-methoxyphenyl)-2-methyl-4H-chromen-4-one (9e)

White crystals (58% yield); mp 212-214° C. (decomp); IR (KBr): $\nu_{max}$ 2958, 1633, 1589, 1438, 1246, 1066 cm$^{-1}$; $^1$H NMR (400 MHz, DMSO-d$_6$): δ 2.28 (s, 3H, 2-CH$_3$), 3.79 (s, 3H, 4'-OCH$_3$), 4.71 (s, 2H, 8-CH$_2$), 4.89 (br. s, 1H, 8-CH$_2$O$\underline{H}$), 6.92-7.05 (m, 3H, 6, 3', 5'-H), 7.19 (d, 2H, $^3$J=8.8 Hz, 2', 6'-H), 7.82 (d, 1H, $^3$J=8.8 Hz, 5-H), 10.68 ppm (s, 1H, 7-OH); $^{13}$C NMR (125 MHz, DMSO-d$_6$): δ 19.18, 51.48, 55.02, 113.43, 114.13, 114.55, 115.51, 121.43, 125.33, 125.64, 131.62, 155.27, 158.47, 160.30, 162.37, 175.19 ppm; MS (CI): m/z (%) 313.1 (MH$^+$, 100). Anal. Calcd. for $C_{18}H_{16}O_5$: C, 69.22; H, 5.16. Found: C, 68.95; H, 5.31.

General Procedures for the Synthesis of Alkoxymethyl Derivatives 10a-10b or 11a-11e.

A mixture of diacetate 8a-8c or 9a-9f (2 mmol) and 0.1 mL of concentrated hydrochloric acid in 10 mL of methanol was refluxed for 16-24 h. The mixture was cooled and diluted with water, and the resulting precipitate was collected by filtration. The products were purified by chromatography using 1:20 methanol-dichloromethane.

5-Hydroxy-7-methoxy-6-(methoxymethyl)-3-(2-methoxyphenyl)-4H-chromen-4-one (10a)

White solid (53% yield); mp 123-124° C.; IR (KBr): $\nu_{max}$ 2934, 2880, 1656, 1585, 1494, 1450, 1284, 1220, 1137, 1078 cm$^{-1}$; $^1$H NMR (400 MHz, DMSO-d$_6$): δ 3.23 (s, 3H, 6-CH$_2$OC$\underline{H}_3$), 3.75 (s, 3H, 2'-OCH$_3$), 3.93 (s, 3H, 7-OCH$_3$), 4.41 (s, 2H, 6-C$\underline{H}_2$OCH$_3$), 6.78 (s, 1H, 8-H), 6.94-7.09 (m, 2H, 3', 5'-H), 7.28-7.34 (m, 1H, 6'-H), 7.35-7.43 (m, 1H, 4'-H), 8.37 (s, 1H, 2-H), 13.24 (s, 1H, 5-OH); $^{13}$C NMR (101 MHz, CDCl$_3$): δ 55.70, 56.17, 58.14, 61.58, 89.56, 106.10, 109.02, 111.26, 119.49, 120.57, 121.46, 130.12, 131.53, 154.23, 157.43, 157.99, 160.95, 164.22, 180.45; MS (CI): m/z 343.3 (MH$^+$, 100). Anal. Calcd. for $C_{19}H_{18}O_6$: C, 66.66; H, 5.30. Found: C, 66.58; H, 5.17.

5-Hydroxy-7-methoxy-6-(methoxymethyl)-3-(4-methoxyphenyl)-4H-chromen-4-one (10b)

White solid (95% yield); mp 180-181° C.; IR (KBr): $\nu_{max}$ 2969, 2835, 1655, 1622, 1579, 1516, 1264, 1225, 1138, 1097 cm$^{-1}$; $^1$H NMR (400 MHz, DMSO-d$_6$): δ 3.24 (s, 3H, 6-CH$_2$OC$\underline{H}_3$), 3.81 (s, 3H, 4'-OCH$_3$), 3.93 (s, 3H, 7-OCH$_3$), 4.43 (s, 2H, 6-C$\underline{H}_2$OCH$_3$), 6.74 (s, 1H, 8-H), 7.01 (d, 2H, $^3$J=8.8 Hz, 3', 5'-H), 7.53 (d, 2H, $^3$J=8.8 Hz, 2', 6'-H), 8.46 (s, 1H, 2-H), 13.29 ppm (s, 1H, 5-OH); $^{13}$C NMR (101 MHz, DMSO-d$_6$): δ 55.16, 56.50, 57.28, 60.84, 90.31, 105.06, 108.41, 113.72, 122.33, 122.68, 130.17, 154.67, 157.45, 159.22, 159.97, 164.11, 180.40 ppm; MS (CI): m/z 343.2 (MH$^+$, 100). Anal. Calcd. for $C_{19}H_{18}O_6$: C, 66.66; H, 5.30. Found: C, 66.87; H, 5.56.

7-Hydroxy-6-(methoxymethyl)-3-(4-methoxyphenyl)-8-methyl-4H-chromen-4-one (10c)

White crystals (68% yield); mp 143-145° C.; IR (KBr): $\nu_{max}$ 2929, 1636, 1580, 1512, 1231, 1174, 1112, 1084 cm$^{-1}$; $^1$H NMR (400 MHz, DMSO-d$_6$): δ 2.30 (s, 3H, 8-CH$_3$), 3.36 (s, 3H, 6-CH$_2$OC$\underline{H}_3$), 3.79 (s, 3H, 4'-OCH$_3$), 4.52 (s, 3H, 6-C$\underline{H}_2$OCH$_3$), 6.99 (d, 2H, $^3$J=8.8 Hz, 3', 5'-H), 7.51 (d, 2H, $^3$J=8.8 Hz, 2', 6'-H), 7.89 (s, 1H, 5-H), 8.42 (s, 1H, 2-H), 9.79 ppm (s, 1H, 7-OH); $^{13}$C NMR (100 MHz, DMSO-d$_6$): δ 8.61, 55.12, 57.79, 69.15, 111.47, 113.52, 116.49, 122.24, 122.72, 124.24, 124.26, 130.00, 153.12, 154.56, 157.15, 158.81, 174.89 ppm; MS (CI): m/z 327.1 (MH$^+$, 100). Anal. Calcd. for $C_{19}H_{18}O_5$: C, 69.93; H, 5.56. Found: C, 70.11; H, 5.38.

5-Hydroxy-7-methoxy-8-(methoxymethyl)-3-(2-methoxyphenyl)-4H-chromen-4-one (11a)

White solid (28% yield); mp 154-155° C.; IR (KBr): $\nu_{max}$ 2922, 2835, 1664, 1558, 1377, 1311, 1285, 1239, 1095, 1031 cm$^{-1}$; $^1$H NMR (400 MHz, DMSO-d$_6$): δ 3.25 (s, 3H, 8-CH$_2$OC$\underline{H}_3$), 3.74 (s, 3H, 2'-OCH$_3$), 3.93 (s, 3H, 7-OCH$_3$), 4.51 (s, 2H, 8-C$\underline{H}_2$OCH$_3$), 6.61 (s, 1H, 6-H), 6.98-7.05 (m, 1H, 5'-H), 7.07-7.15 (m, 1H, 3'-H), 7.24-7.31 (m, 1H, 6'-H), 7.36-7.44 (m, 1H, 4'-H), 8.37 (s, 1H, 2-H), 13.14 ppm (s, 1H, 5-OH); $^{13}$C NMR (101 MHz, DMSO-d$_6$): δ 55.51, 56.49, 57.23, 60.89, 95.23, 104.03, 104.45, 111.23, 119.37, 120.04, 120.28, 129.88, 131.45, 155.31, 155.56, 157.29, 162.04, 163.65, 180.10 ppm; MS (CI): m/z 343.3 (MH$^+$, 100). Anal. Calcd. for $C_{19}H_{18}O_6$; C, 66.66; H, 5.30. Found: C, 66.93; H, 5.12.

5-Hydroxy-7-methoxy-8-(methoxymethyl)-3-(4-methoxyphenyl)-4H-chromen-4-one (11b)

White solid (41% yield); mp 126-128° C.; IR (KBr): $\nu_{max}$ 2938, 2838, 1662, 1610, 1585, 1541, 1246, 1204, 1072, 1042 cm$^{-1}$; $^1$H NMR (400 MHz, DMSO-d$_6$): δ 3.25 (s, 3H, 8-CH$_2$OC$\underline{H}_3$), 3.79 (s, 3H, 4'-OCH$_3$), 3.92 (s, 3H, 7-OCH$_3$), 4.50 (s, 2H, 8-C$\underline{H}_2$OCH$_3$), 6.60 (s, 1H, 6-H), 7.01 (d, 2H, J=8.8 Hz, 3', 5'-H), 7.52 (d, 2H, $^3$J=8.8 Hz, 2', 6'-H), 8.51 (s, 1H, 2-H), 13.24 ppm (s, 1H, 5-OH); $^{13}$C NMR (101 MHz, DMSO-d$_6$): δ 55.16, 56.53, 57.28, 60.92, 95.30, 103.96, 104.65, 113.72, 121.85, 122.66, 130.17, 154.76, 155.38, 159.19, 162.36, 163.81, 180.64 ppm; MS (CI): m/z 343.3 (MH$^+$, 100). Anal. Calcd. for $C_{19}H_{18}O_6$: C, 66.66; H, 5.30. Found: C, 66.43; H, 5.22.

7-Hydroxy-8-(methoxymethyl)-3-(2-methoxyphenyl)-4H-chromen-4-one (11c)

White crystals (78% yield); mp 164-166° C.; IR (KBr): $\nu_{max}$ 2937, 1624, 1579, 1427, 1284, 1259 cm$^{-1}$; $^1$H NMR (400 MHz, DMSO-d$_6$): δ 3.29 (s, 3H, 8-CH$_2$OC$\underline{H}_3$), 3.71 (s, 3H, 2'-OCH$_3$), 4.62 (s, 2H, 8-C$\underline{H}_2$OCH$_3$), 6.91-7.02 (m, 2H, 6, 5'-H), 7.04-7.10 (m, 1H, 3'-H), 7.20-7.24 (m, 1H, 6'-H), 7.33-7.40 (m, 1H, 4'-H), 7.82 (d, 1H, $^3$J=8.8 Hz, 5-H), 8.17 ppm (s, 1H, H-2); $^{13}$C NMR (125 MHz, DMSO-d$_6$): δ 55.07, 57.45, 61.37, 111.24, 113.55, 114.45, 116.53, 122.95, 124.13, 126.70, 130.01, 153.03, 156.16, 158.92, 161.10, 174.71 ppm; MS (CI): m/z 313.2 (MH$^+$, 100). Anal. Calcd. for $C_{18}H_{16}O_5$: C, 69.22; H, 5.16. Found: C, 68.88; H, 5.27.

7-Hydroxy-8-(methoxymethyl)-3-(4-methoxyphenyl)-4H-chromen-4-one (11d)

White crystals (89% yield); mp 167-169° C. decomp; IR (KBr): $\nu_{max}$ 2937, 1624, 1579, 1427, 1284, 1259 cm$^{-1}$; $^1$H NMR (400 MHz, DMSO-d$_6$): δ 3.30 (s, 3H, 8-CH$_2$OC$\underline{H}_3$), 3.79 (s, 3H, 4'-OCH$_3$), 4.62 (s, 2H, 8-C$\underline{H}_2$OCH$_3$), 6.99 (d, 2H, $^3$J=8.8 Hz, 3', 5'-H), 7.05 (d, 1H, $^3$J=8.8 Hz, 6-H), 7.53 (d, 2H, $^3$J=8.8 Hz, 2', 6'-H), 7.98 (d, 1H, $^3$J=8.8 Hz, 5-H), 8.40 (s, 1H,2-H), 10.83 ppm (s, 1H, 2-H) ppm; $^{13}$C NMR (125 MHz, DMSO-d$_6$): δ 55.07, 57.45, 61.37, 111.24, 113.55, 114.45, 116.53, 122.95, 124.13, 126.70, 130.01, 153.03, 156.16, 158.92, 161.10, 174.71 ppm; MS (CI): m/z 313.1 (MH$^+$, 100). Anal. Calcd. for $C_{18}H_{16}O_5$: C, 69.22; H, 5.16. Found: C, 69.01; H, 4.92.

7-Hydroxy-8-(methoxymethyl)-3-(4-methoxyphenyl)-2-methyl-4H-chromen-4-one (11e)

White crystals (89% yield); mp 215-217° C. decomp; IR (KBr): $\nu_{max}$ 2927, 1614, 1585, 1406, 1294, 1246, 1065 cm$^{-1}$; $^1$H NMR (400 MHz, DMSO-d$_6$): δ 2.27 (s, 3H, 2-CH$_3$), 3.29 (s, 3H, 8-CH$_2$OC$\underline{H}_3$), 3.79 (s, 3H, 4'-OCH$_3$), 4.61 (s, 2H, 8-C$\underline{H}_2$OCH$_3$), 6.98 (d, 2H, $^3$J=8.8 Hz, 3', 5'-H), 7.00 (d, 1H, $^3$J=8.8 Hz, 6-H), 7.20 (d, 2H, $^3$J=8.8 Hz, 2', 6'-H), 7.87 (d, 1H, $^3$J=8.8 Hz, 5-H), 10.85 ppm (s, 1H) ppm; $^{13}$C NMR (125 MHz, DMSO-d$_6$): δ 19.13, 55.01, 57.48, 61.40, 110.99, 113.41, 114.03, 115.43, 121.52, 125.21, 126.48, 131.60, 155.70, 158.48, 160.89, 162.25, 175.08 ppm; MS (CI): m/z 327.1 (MH$^+$, 100). Anal. Calcd. for $C_{19}H_{18}O_5$: C, 69.93; H, 5.56. Found: C, 70.23; H, 5.28.

Cell Proliferation Assay:

PC3 prostate cancer cells were cultured in DMEM/F-12 HAM Mixture (Sigma D8437), 10% Fetal Bovine Serum (Atlanta Biological S11150). Before the treatment, 3.5×10$^4$ cells per well were split into 12-well plates. After 24 h, 10 μM of each compound was added to each well. DMSO was used as a control. This experiment was done in triplicate. Cell viability and number were analyzed using Vi-Cell XR Cell Viability Analyzer (Beckman Coulter).

General Procedure for the Synthesis of Betti Bases 15 and 17.

To a stirred suspension of 14 or 16 (2 mmol) in 10 mL of isopropanol was added 0.3 mL (2.2 mmol, 1.1 eq) of bis(N,N-dimethylamino)methane at 70° C. The mixture was heated at 80° C. for 2 h and cooled to afford a precipitate that was collected by gravity filtration. In the absence of crystallization, the residue was triturated with hexane to induce crystallization. The Betti bases 14 and 16 were re-crystallized from isopropanol-hexane.

8-[(N,N-Dimethylamino)methyl]-7-hydroxy-3-(4-methoxyphenyl)-4H-chromen-4-one (15a)

Pale yellow solid (83% yield); mp 174-176° C.; IR (KBr) $\nu_{max}$ 3448, 2951, 1626, 1427, 1246, 1178, 1028 cm$^{-1}$; $^1$H NMR (400 MHz, CDCl$_3$) δ 2.44 (s, 6H, N(CH$_3$)$_2$), 3.85 (s, 3H, 4'-OCH$_3$), 3.99 (s, 2H, 8-CH$_2$), 6.90 (d, 1H, $^3$J=8.8 Hz, 6-H), 6.97 (d, 2H, $^3$J=8.8 Hz, 3', 5'-H), 7.50 (d, 2H, $^3$J=8.8 Hz, 2', 6'-H), 7.89 (s, 1H, 2-H), 8.14 (d, 1H, $^3$J=8.8 Hz, 5-H), 10.21 ppm (br s, 1H, 7-OH); $^{13}$C NMR (125 MHz, CDCl$_3$) δ 44.41, 54.87, 55.20, 107.27, 113.80, 115.44, 116.89, 124.22, 124.32, 126.67, 130.00, 151.25, 154.96, 159.41, 163.97, 175.74 ppm; MS (CI): m/z 326.1 (MH$^+$, 100). Anal. Calcd for $C_{19}H_{19}NO_4$: C, 70.14; H, 5.89; N, 4.30. Found: C, 69.88; H, 5.97; N, 4.39.

3-(3,4-Dimethoxyphenyl)-8-[(N,N-dimethylamino)methyl]-7-hydroxy-4H-chromen-4-one (15b)

Pale yellow solid (77% yield); mp 154-155° C.; IR (KBr) $\nu_{max}$ 2948, 1636, 1602, 1517, 1266, 1145, 1024 cm$^{-1}$; $^1$H NMR (400 MHz, CDCl$_3$) δ 2.44 (s, 6H, N(CH$_3$)$_2$), 3.91, 3.93 (2s, 6H, 3', 4'-OCH$_3$), 3.99 (s, 2H, 8-CH$_2$), 6.86-6.96 (m, 2H, 6, 6'-H), 7.00-7.07 (m, 1H, 5'-H), 7.18-7.23 (m, 1H, 2'-H), 7.92 (s, 1H, 2-H), 8.13 (d, 1H, $^3$J=8.8 Hz, 5-H), 9.79 ppm (s, 1H, 7-OH); $^{13}$C NMR (125 MHz, CDCl$_3$) δ 44.52, 55.04, 55.88, 55.89, 107.40, 111.04, 112.46, 115.58, 116.93, 120.90, 124.45, 124.70, 126.68, 148.64, 148.95, 151.44, 154.93, 164.05, 175.86 ppm; MS (CI): m/z 356.2 (MH$^+$, 100). Anal. Calcd for $C_{20}H_{21}NO_5$: C, 67.59; H, 5.96; N, 3.94. Found: C, 67.88; H, 5.97; N, 4.39.

3-(1,3-Benzodioxol-5-yl)-8-[(N,N-dimethylamino)methyl]-7-hydroxy-4H-chromen-4-one (15c)

Pale yellow solid (73% yield); mp 160-161° C.; IR (KBr) $\nu_{max}$ 2960, 2987, 1639, 1488, 1425, 1246, 1017 cm$^{-1}$; $^1$H NMR (400 MHz, CDCl$_3$) δ 2.44 (s, 6H, N(CH$_3$)$_2$), 3.98 (s, 2H, 8-CH$_2$), 5.98 (s, 2H, 3',4'-OCH$_2$O), 6.80-7.00 (m, 3H, 6, 5', 6'-H), 7.06-7.13 (m, 1H, 2'-H), 7.86 (s, 1H, 2-H), 8.11 (d, 1H, $^3$J=8.8 Hz, 5-H), 9.95 ppm (s, 1H, 7-OH); $^{13}$C NMR (125 MHz, CDCl$_3$) δ 44.60, 55.15, 101.13, 107.49, 108.34, 109.78, 115.62, 116.94, 122.34, 124.61, 125.78, 126.78, 147.56, 147.62, 151.46, 154.97, 164.12, 175.73 ppm; MS (CI): m/z 340.3 (MH$^+$, 100). Anal. Calcd for $C_{19}H_{17}NO_5$: C, 67.25; H, 5.05; N, 4.13. Found: C, 67.48; H, 4.97; N, 4.39.

3-(2,3-Dihydro-1,4-benzodioxin-6-yl)-8-[(N,N-dimethylamino)methyl]-7-hydroxy-4H-chromen-4-one (15d)

Pale yellow solid (68% yield); mp 179-180° C.; IR (KBr); $\nu_{max}$ 3072, 2955, 1643, 1602, 1509, 1289, 1060, 1027 cm$^{-1}$; $^1$H NMR (400 MHz, CDCl$_3$) δ 2.42 (s, 6H, N(CH$_3$)$_2$), 3.97 (s, 2H, 8-CH$_2$), 4.27 (s, 4H, 3',4'-OCH$_2$CH$_2$O), 6.88 (d, 1H, $^3$J=8.7 Hz, 6-H), 6.91 (d, 1H, $^3$J=8.4 Hz, 8'-H), 7.02 (dd, 1H, $^3$J=8.7 Hz, $^4$J=2.0 Hz, 7'-H), 7.09 (d, 1H, $^4$J=2.0 Hz, 5'-H), 7.86 (s, 1H, 2-H), 8.11 (d, 1H, $^3$J=8.7 Hz, 5-H), 10.04 ppm (s, 1H, 7-OH); $^{13}$C NMR (125 MHz, CDCl$_3$) δ 44.39, 54.63, 64.24, 64.38, 107.04, 115.54, 116.87, 117.16, 117.88, 122.08, 124.27, 125.10, 126.94, 143.32, 143.57, 151.46, 155.02, 164.03, 175.67 ppm; MS (CI): m/z 354.2 (MH$^+$, 100). Anal. Calcd for $C_{20}H_{19}NO_5$: C, 67.98; H, 5.42; N, 3.96. Found: C, 68.10; H, 5.67; N, 4.79.

3-(4-Chlorophenyl)-8-[(N,N-dimethylamino)methyl]-7-hydroxy-4H-chromen-4-one (15e)

Pale yellow solid (78% yield); mp 174-176° C.; IR (KBr) $v_{max}$ 3061, 2958, 2838, 1881, 1632, 1590, 1466, 1378, 1257, 1204, 1176, 1011, 824 cm$^{-1}$; $^1$H NMR (400 MHz, CDCl$_3$) δ 2.43 (s, 6H, N(CH$_3$)$_2$), 3.97 (s, 2H, 8-CH$_2$), 6.90 (d, 1H, $^3$J=8.8 Hz, 6-H), 7.36-7.41 (m, 2H, 3', 5'-H), 7.46-7.52 (m, 2H, 2', 6'-H), 7.89 (s, 1H, H-2), 8.11 (d, 1H, $^3$J=8.8 Hz, 5-H), 12.48 ppm (s, 1H, 7-OH); $^{13}$C NMR (100 MHz, CDCl$_3$) δ 44.59, 55.14, 107.55, 115.79, 116.89, 123.84, 126.75, 128.60, 130.21, 130.51, 134.01, 151.79, 155.00, 164.32, 175.37 ppm; MS (CI): m/z 330.2 (MH$^+$, 100), 332.2 (MH$^+$, 28). Anal. Calcd for $C_{18}H_{16}ClNO_3$: C, 65.56; H, 4.89; N, 4.25. Found: C, 65.81; H, 5.07; N, 4.47.

8-[(N,N-Dimethylamino)methyl]-7-hydroxy-2-methyl-3-phenyl-4H-chromen-4-one (15f)

Pale yellow solid (81% yield); mp 168-170° C.; IR (KBr) $v_{max}$ 3052, 2952, 1633, 1599, 1399, 1287, 1258, 1018 cm$^{-1}$; $^1$H NMR (400 MHz, CDCl$_3$) δ 2.29 (s, 3H, 2-CH$_3$), 2.44 (s, 6H, N(CH$_3$)$_2$), 3.98 (s, 2H, 8-CH$_2$), 6.84 (d, 1H, $^3$J=8.8 Hz, 6-H), 7.24-7.47 (m, 5H, 3-Ph), 8.05 (d, 1H, $^3$J=8.8 Hz, 5-H), 11.79 ppm (s, 1H, 7-OH); $^{13}$C NMR (125 MHz, CDCl$_3$) δ 19.32, 44.41, 54.67, 106.69, 115.12, 115.83, 122.95, 126.83, 127.58, 128.24, 130.38, 133.17, 154.73, 161.90, 163.78, 176.29 ppm; MS (CI): m/z 310 (MH$^+$, 100). Anal. Calcd for $C_{19}H_{19}NO_3$: C, 73.77; H, 6.19; N, 4.53. Found: C, 73.92; H, 5.99; N, 4.43.

8-[(N,N-Dimethylamino)methyl]-7-hydroxy-3-(4-methoxyphenyl)-2-methyl-4H-chromen-4-one (15 g)

Pale yellow solid (91% yield); mp 185-187° C. decomp; IR (KBr) $v_{max}$ 3450, 2958, 1626, 1603, 1255, 1176, 1016 cm$^{-1}$; $^1$H NMR (400 MHz, CDCl$_3$): δ 2.30 (s, 3H, 2-CH$_3$), 2.44 (s, 6H, N(CH$_3$)$_2$), 3.84 (s, 3H, 4'-OCH$_3$), 3.98 (s, 2H, 8-CH$_2$), 6.85 (d, 1H, $^3$J=8.8 Hz, 6-H), 6.97 (d, 2H, $^3$J=8.7 Hz, 3', 5'-H), 7.20 (d, 2H, $^3$J=8.7 Hz, 2', 6'-H), 8.04 (d, 1H, $^3$J=8.8 Hz, 5-H), 11.30 ppm (br s, 1H); $^{13}$C NMR (125 MHz, CDCl$_3$): δ 19.28, 44.44, 54.85, 55.21, 106.83, 113.78, 115.03, 115.89, 122.51, 125.33, 126.74, 131.51, 154.68, 158.99, 161.76, 163.69, 176.47 ppm; MS (CI): m/z 340.1 (MH+, 100). Anal. Calcd for $C_{20}H_{21}NO_4$: C, 70.78; H, 6.24; N, 4.13. Found: C, 70.91; H, 5.95; N, 4.33.

3-(3,4-dimethoxyphenyl)-8-[(N,N-dimethylamino)methyl]-7-hydroxy-2-methyl-4H-chromen-4-one (15h)

Pale yellow solid (87% yield); mp 150-152° C.; IR (KBr) $v_{max}$ 2995, 2841, 1635, 1516, 1393, 1262, 1020 cm$^{-1}$; $^1$H NMR (400 MHz, CDCl$_3$): δ 2.31 (s, 3H, 2-CH$_3$), 2.45 (s, 6H, N(CH$_3$)$_2$), 3.87, 3.91 (2s, 6H, 3', 4'-OCH$_3$), 3.99 (s, 2H, 8-CH$_2$), 6.78-6.83 (m, 2H, 2', 6'-H), 6.85 (d, 1H, $^3$J=8.8 Hz, 6-H), 6.92 (d, 1H, $^3$J=8.7 Hz, 5'-H), 8.05 ppm (d, 1H, $^3$J=8.8 Hz, 5-H); $^{13}$C NMR (125 MHz, CDCl$_3$): δ 19.39, 44.62, 55.24, 55.88, 55.89, 107.14, 111.11, 113.67, 115.11, 115.94, 122.76, 122.80, 125.84, 126.64, 148.50, 148.70, 154.61, 161.89, 163.78, 176.50 ppm; MS (CI): m/z 370.3 (MH$^+$, 100). Anal. Calcd for $C_{21}H_{23}NO_5$: C, 68.28; H, 6.28; N, 3.79. Found: C, 67.97; H, 6.14; N, 4.56.

3-(4-Chlorophenyl)-8-[(N,N-dimethylamino)methyl]-7-hydroxy-2-methyl-4H-chromen-4-one (15i)

Pale yellow solid (86% yield); mp 174-175° C.; IR (KBr) $v_{max}$ 2974, 2835, 1631, 1407, 1371, 1285, 1258, 1014 cm$^{-1}$; $^1$H NMR (400 MHz, CDCl$_3$) δ 2.29 (s, 3H, 2-CH$_3$), 2.44 (s, 6H, N(CH$_3$)$_2$), 3.98 (s, 2H, 8-CH$_2$), 6.86 (d, 1H, $^3$J=8.8 Hz, 6-H), 7.19-7.25 (m, 2H, 3', 5'-H), 7.36-7.42 (m, 2H, 2', 6'-H), 8.03 (d, 1H, $^3$J=8.8 Hz, 5-H), 12.14 ppm (s, 7-OH); $^{13}$C NMR (100 MHz, CDCl$_3$) δ 19.32, 44.63, 55.24, 107.18, 115.29, 115.80, 121.99, 126.65, 128.54, 131.76, 131.88, 133.61, 154.63, 161.76, 163.99, 176.03 ppm; MS (CI): m/z 344.3 (MH$^+$, 100), 346.3 (MH$^+$, 29). Anal. Calcd for $C_{19}H_{18}ClNO_3$: C, 66.38; H, 5.28; N, 4.07. Found: C, 66.10; H, 4.99; N, 3.85.

6-[(N,N-Dimethylamino)methyl]-7-hydroxy-3-(4-methoxyphenyl)-8-methyl-4H-chromen-4-one (17a)

To a suspension of 2 mmol of 16a in 10 mL of 2-methoxyethanol was added 1 mL (7.4 mmol) of bis(N,N-dimethylamino)methane at 70° C. The mixture was heated at 124° C. for 16 h, cooled, and diluted with hexane. The precipitate was collected to afford 672 mg (99%) of 17a as a yellow solid: mp 182-183° C.; IR (KBr) $v_{max}$ 3069, 2954, 2831, 1627, 1512, 1461, 1369, 1290, 1223, 1176, 830 cm-1; $^1$H NMR (400 MHz, CDCl$_3$) δ 2.32 (s, 3H, 8-CH$_3$), 2.37 (s, 6H, N(CH$_3$)$_2$), 3.78 (s, 2H, 6-CH$_2$), 3.84 (s, 3H, 4'-OCH$_3$), 6.97 (d, 2H, $^3$J=8.7 Hz, 3', 5'-H), 7.50 (d, 2H, $^3$J=8.7 Hz, 2', 6'-H), 7.81 (s, 1H, 5-H), 7.97 (s, 1H, 2-H), 9.81 ppm (br s, 1H, 7-OH); $^{13}$C NMR (125 MHz, CDCl$_3$) δ 7.81, 44.21, 55.30, 62.37, 111.80, 113.88, 116.63, 120.31, 122.69, 124.02, 124.60, 130.07, 152.01, 155.76, 159.38, 161.30, 176.30 ppm; MS (CI): m/z 340.3 (MH$^+$, 100). Anal. Calcd for $C_{20}H_{21}NO_4$: C, 70.87; H, 6.24; N, 4.13. Found: C, 70.62; H, 6.43; N, 4.11.

6-[(N,N-Dimethylamino)methyl]-7-hydroxy-3-(4-methoxyphenyl)-2,8-dimethyl-4H-chromen-4-one (17g)

The procedure described for 17a was repeated to afford 509 mg of 17g as white solid (72% yield); mp 176-177° C.; IR (KBr) $v_{max}$ 3039, 2952, 2834, 1643, 1606, 1511, 1397, 1239, 1158 cm$^{-1}$; $^1$H NMR (400 MHz, CDCl$_3$) δ 2.32 (s, 6H, 2, 8-CH$_3$), 2.36 (s, 6H, N(CH$_3$)$_2$), 3.76 (s, 2H, 6-CH$_2$), 3.85 (s, 3H, 4'-OCH$_3$), 6.97 (d, 2H, $^3$J=8.7 Hz, 3', 5'-H), 7.21 (d, 2H, $^3$J=8.7 Hz, 2', 6'-H), 7.74 ppm (s, 1H, 5-H); $^{13}$C NMR (125 MHz, CDCl$_3$) δ 7.83, 19.43, 44.20, 55.23, 62.34, 111.39, 113.77, 115.55, 119.84, 122.14, 122.62, 125.67, 131.55, 155.31, 158.87, 161.02, 162.34, 176.92 ppm; MS (CI): m/z 354.2 (MH$^+$, 100). Anal. Calcd. for $C_{21}H_{23}NO_4$: C, 71.37; H, 6.56; N, 3.96. Found: C, 71.46; H, 6.31; N, 4.17.

General Procedure for the Synthesis of Diels-Alder Adducts 20 or 25.

To a solution of 2 mmol of 15 or 17 in 10 mL of N,N-dimethylformamide was added 2 mL (26 mmol, 13 eq) of 2,3-dihydrofuran. The solution was refluxed for 24-40 h. The solvent and excess 2,3-dihydrofuran were evaporated in vacuo, and the residue was purified by chromatography using 1:50 methanol-dichloromethane to afford adducts 20 or 25.

3-(4-Methoxyphenyl)-9,10,10a,11-tetrahydro-4H,7aH-furo[2,3-b]pyrano[2,3-f]chromen-4-one (20a)

Pale yellow solid (70% yield); mp 201-202° C.; IR (KBr) $v_{max}$ 2903, 2844, 1643, 1610, 1510, 1435, 1295, 1242, 1205, 1052 cm$^{-1}$; $^1$H NMR (400 MHz, CDCl$_3$) δ1.69-1.82 (m, 1H, 10α-CH), 2.10-2.20 (m, 1H, 10β-CH), 2.75-2.86 (m, 1H, 10α-CH), 3.09 (dd, 1H, $^2$J=17.5 Hz, $^3$J=6.2 Hz, 11α-CH), 3.19 (dd, 1H, $^2$J=17.5 Hz, $^3$J=2.0 Hz, 11β-CH), 3.85 (s, 3H, 4'-OMe), 4.01-4.10 (m, 1H, 9α-CH), 4.16-4.24 (m, 1H, 9β-CH), 5.68 (d, 1H, $^3$J=4.2 Hz, 7α-CH), 6.94 (d, 1H, $^3$J=8.8 Hz, 6-H), 6.96-7.00 (m, 2H, 3', H-5'-H), 7.48-7.54 (m, 2H, 2', H-6'-H), 7.96 (s, 1H, 2-H), 8.10 ppm (d, 1H, $^3$J=8.8 Hz, 5-H); $^{13}$C NMR (400 MHz, CDCl$_3$) δ 19.46, 27.72, 36.27, 55.34, 68.45, 100.86, 107.02, 113.95, 115.55, 118.49, 124.19, 124.79, 125.49, 130.11, 151.74, 155.39, 157.14, 159.57, 175.95 ppm; MS (CI): m/z 351.2 (MH$^+$, 100). Anal. Calcd. for C$_{21}$H$_{18}$O$_5$: C, 71.99; H, 5.18. Found: C, 72.17; H, 4.92.

3-(3,4-Dimethoxyphenyl)-9,10,10a,11-tetrahydro-4H,7aH-furo[2,3-b]pyrano[2,3-f]chromen-4-one (20b)

Pale yellow solid (29% yield); mp 193-195° C.; IR (KBr) ν$_{max}$ 2900, 2843, 1637, 1607, 1510, 1437, 1398, 1290, 1244, 1057, 1025, 840 cm$^{-1}$; $^1$H NMR (400 MHz, CDCl$_3$) δ 1.68-1.82 (m, 1H, 10α-CH), 2.10-2.21 (m, 1H, 10β-CH), 2.75-2.86 (m, 1H, 10a-CH), 3.09 (dd, 1H, $^2$J=17.5, $^3$J=6.0 Hz, 11α-CH), 3.14-3.24 (m, 1H, 11β-CH), 3.92 (s, 3H, 3'-OMe), 3.93 (s, 3H, 4'-OMe), 4.01-4.12 (m, 1H, 9α-CH), 4.15-4.24 (m, 1H, 9β-CH), 5.68 (d, 1H, $^3$J=4.1 Hz, 7α-CH), 6.91-6.98 (m, 2H, 6, 5'-H), 7.03-7.09 (m, 1H, 6'-H), 7.22 (1H, $^4$J=1.8 Hz, 2'-H), 7.99 (s, 1H, 2-H), 8.10 ppm (d, 1H, $^3$J=8.9 Hz, 5-H); $^{13}$C NMR (400 MHz, CDCl$_3$) δ 19.47, 27.71, 36.26, 55.96, 55.99, 68.46, 100.87, 107.03, 111.15, 112.52, 115.65, 118.47, 121.01, 124.62, 124.85, 125.47, 148.76, 149.10, 151.94, 155.38, 157.21, 176.00 ppm; MS (CI): m/z 381.2 (MH$^+$, 100). Anal. Calcd for C$_{22}$H$_{20}$O$_6$: C, 69.46; H, 5.30. Found: C, 69.21; H, 5.01.

3-(1,3-Benzodioxol-5-yl)-9,10,10a,11-tetrahydro-4H,7aH-furo[2,3-b]pyrano[2,3-f]chromen-4-one (20c)

Pale yellow solid (64% yield); mp 203-205° C.; IR (KBr) ν$_{max}$ 2986, 2903, 1641, 1600, 1490, 1435, 1245, 1226, 1056, 1032 cm$^{-1}$; $^1$H NMR (400 MHz, CDCl$_3$) δ 1.67-1.81 (m, 1H, 10α-CH), 2.10-2.20 (m, 1H, 10β-CH), 2.75-2.86 (m, 1H, 10a-CH), 3.09 (dd, 1H, $^2$J=17.6, $^3$J=6.2 Hz, 11α-CH), 3.19 (dd, 1H, $^2$J=17.6, $^3$J=2.0 Hz, 11β-CH), 4.00-4.11 (m, 1H, 9α-CH), 4.14-4.24 (m, 1H, 9β-CH), 5.68 (d, 1H, $^3$J=4.2 Hz, 7α-CH), 6.00 (s, 2H, OCH$_2$O), 6.87 (d, 1H, $^3$J=8.0 Hz, 7'-H), 6.94 (d, 1H, $^3$J=8.8 Hz, 6-H), 6.98 (dd, 1H, $^3$J=8.0, $^4$J=1.7 Hz, 6'-H), 7.10 (d, 1H, $^3$J=1.7 Hz, 4'-H), 7.95 (s, 1H, 2-H), 8.09 ppm (d, 1H, $^3$J=8.8 Hz, 5-H); $^{13}$C NMR (400 MHz, CDCl$_3$) δ 19.46, 27.71, 36.26, 68.46, 100.87, 101.16, 107.04, 108.36, 109.75, 115.63, 118.41, 122.35, 124.93, 125.50, 125.64, 147.63, 147.66, 151.91, 155.37, 157.21, 175.79 ppm; MS (CI): m/z 365.1 (MH$^+$, 100). Anal. Calcd. for C$_{21}$H$_{16}$O$_6$: C, 69.23; H, 4.43. Found: C, 69.52; H, 4.18.

3-(2,3-Dihydro-1,4-benzodioxin-6-yl)-9,10,10a,11-tetrahydro-4H,7aH-furo[2,3-b]pyrano[2,3-f]chromen-4-one (20d)

Pale yellow solid (75% yield); mp 188-189° C.; IR (KBr) ν$_{max}$ 2936, 2862, 1656, 1611, 1512, 1437, 1281, 1219, 1198, 1138 cm$^{-1}$; $^1$H NMR (400 MHz, CDCl$_3$) δ 1.68-1.82 (m, 1H, 10α-CH), 2.09-2.20 (m, 1H, 10β-CH), 2.75-2.86 (m, 1H, 10a-CH), 3.09 (dd, 1H, $^2$J=17.4, $^3$J=6.4 Hz, 11α-CH), 3.19 (dd, 1H, $^2$J=17.4, $^3$J=2.0 Hz, 11β-CH), 3.99-4.09 (m, 1H, 9α-CH), 4.14-4.23 (m, 1H, 9β-CH), 4.25-4.32 (m, 4H, OCH$_2$CH$_2$O), 5.68 (d, 1H, $^3$J=4.2 Hz, 7a-CH), 6.90-6.96 (m, 2H, 6, 8'-H), 7.04 (dd, 1H, $^3$J=8.3, $^4$J=2.0 Hz, 7'-H), 7.11 (d, 1H, $^3$J=2.0 Hz, 2'-H), 7.94 (s, 1H, 7-H), 8.09 ppm (d, 1H, $^3$J=8.8 Hz, 5-H); $^{13}$C NMR (400 MHz, CDCl$_3$) δ 19.45, 27.70, 36.25, 64.32, 64.46, 68.45, 100.87, 107.05, 115.55, 117.25, 117.94, 118.46, 122.13, 124.63, 125.09, 125.48, 143.42, 143.69, 151.92, 155.35, 157.15, 175.79 ppm; MS (CI): m/z 379.2 (MH$^+$, 100). Anal. Calcd. for C$_{22}$H$_{18}$O$_6$: C, 69.84; H, 4.79. Found: C, 70.07; H, 4.95.

3-(4-Chlorophenyl)-9,10,10a,11-tetrahydro-4H,7aH-furo[2,3-b]pyrano[2,3-f]chromen-4-one (20e)

Pale yellow solid (55% yield); mp 194-195° C.; IR (KBr) ν$_{max}$ 2961, 2899, 1637, 1598, 1492, 1438, 1377, 1244, 1092, 1064, 1012, 819 cm$^{-1}$; $^1$H NMR (400 MHz, CDCl$_3$) δ 1.70-1.82 (m, 1H, 10α-CH), 2.12-2.21 (m, 1H, 10β-CH), 2.77-2.86 (m, 1H, 10a-CH), 3.09 (dd, 1H, $^2$J=17.5, $^3$J=6.3 Hz, 11α-CH), 3.19 (dd, 1H, $^2$J=17.5, $^3$J=2.0 Hz, 11β-CH), 4.02-4.11 (m, 1H, 9α-CH), 4.16-4.25 (m, 1H, 9β-CH), 5.69 (d, 1H, $^3$J=4.2 Hz, 7a-CH), 6.96 (d, 1H, $^3$J=8.9 Hz, 6-H), 7.39-7.44 (m, 2H, 3', 5'-H), 7.49-7.55 (m, 2H, 2', 6'-H), 7.99 (s, 1H, 2-H), 8.10 ppm (d, 1H, $^3$J=8.9 Hz, 5-H); $^{13}$C NMR (400 MHz, CDCl$_3$) δ 19.46, 27.70, 36.22, 68.48, 100.90, 107.10, 115.83, 118.38, 124.19, 125.50, 128.65, 130.22, 130.36, 134.15, 152.27, 155.42, 157.40, 175.50 ppm; MS (CI): m/z 355.2 (MH$^+$, 100), 357.1 (MH$^+$, 30). Anal. Calcd for C$_{20}$H$_{15}$ClO$_4$: C, 67.71; H, 4.26. Found: C, 67.55; H, 4.43.

2-Methyl-3-phenyl-9,10,10a,11-tetrahydro-4H,7aH-furo[2,3-b]pyrano[2,3-f]chromen-4-one (20f)

Pale yellow solid (73% yield); mp 181-182° C.; IR (KBr) ν$_{max}$ 2966, 2900, 1634, 1607, 1579, 1510, 1437, 1398, 1244, 1057, 840 cm$^{-1}$; $^1$H NMR (400 MHz, CDCl$_3$) δ 1.70-1.83 (m, 1H, 10α-CH), 2.11-2.21 (m, 1H, 10β-CH), 2.32 (s, 3H, 2-CH$_3$), 2.75-2.85 (m, 1H, 10a-CH), 3.10 (dd, 1H, $^2$J=17.4, $^3$J=6.1 Hz, 11α-CH), 3.21 (dd, 1H, $^2$J=17.4, $^3$J=2.0 Hz, 11β-CH), 4.01-4.10 (m, 1H, 9α-CH), 4.16-4.23 (m, 1H, 9β-CH), 5.68 (d, 1H, $^3$J=4.2 Hz, 7a-CH), 6.91 (d, 1H, $^3$J=8.8 Hz, 6-H), 7.27-7.30 (m, 2H, 2', 6'-H), 7.46-7.34 (m, 3H, 3', 4', 5', H), 8.02 ppm (d, 1H, $^3$J=8.8 Hz, 5-H); $^{13}$C NMR (400 MHz, CDCl$_3$) δ 19.39, 19.52, 27.76, 36.31, 68.44, 100.84, 106.71, 115.15, 117.44, 123.38, 125.40, 127.68, 128.33, 130.42, 133.20, 155.01, 157.00, 162.28, 176.34 ppm; MS (CI): m/z 335.2 (MH$^+$, 100). Anal. Calcd for C$_{21}$H$_{18}$O$_4$: C, 75.43; H, 5.43. Found: C, 75.85; H, 5.72.

3-(4-Methoxyphenyl)-2-methyl-9,10,10a,11-tetrahydro-4H,7aH-furo[2,3-b]pyrano[2,3-f]chromen-4-one (20g)

Pale yellow solid (62% yield); mp 227-229° C.; IR (KBr) ν$_{max}$ 2900, 2825, 1634, 1607, 1510, 1437, 1398, 1290, 1244, 1057, 1025 cm$^{-1}$; $^1$H NMR (400 MHz, CDCl$_3$) δ 1.68-1.82 (m, 1H, 10α-CH), 2.09-2.20 (m, 1H, 10β-CH), 2.33 (s, 3H, 2-CH$_3$), 2.74-2.85 (m, 1H, 10a-CH), 3.09 (dd, 1H, $^2$J=17.4, $^3$J=6.2 Hz, 11α-CH), 3.19 (dd, 1H, $^2$J=17.4, $^3$J=1.6 Hz, 11β-CH), 3.85 (s, 3H, 4'-OMe), 4.00-4.09 (m, 1H, 9α-CH), 4.15-4.22 (m, 1H, 9β-CH), 5.67 (d, 1H, $^3$J=4.2 Hz, 7a-CH), 6.90 (d, 1H, $^3$J=8.8 Hz, 6-H), 6.97 (d, 2H, $^3$J=8.7 Hz, 3', 5'-H), 7.21 (d, 2H, $^3$J=8.7 Hz, 2', 6'-H), 8.01 ppm (d, 1H, $^3$J=8.8 Hz, 5-H); $^{13}$C NMR (400 MHz, CDCl$_3$) δ 19.41, 19.53, 27.78, 36.33, 55.29, 68.43, 100.84, 106.69, 113.87, 115.08, 117.43, 122.92, 125.31, 125.42, 131.55, 154.98,

3-(3,4-Dimethoxyphenyl)-2-methyl-9,10,10a,11-tetrahydro-4H,7aH-furo[2,3-b]pyrano[2,3-f]chromen-4-one (20h)

Pale yellow solid (56% yield); mp 217-219° C.; IR (KBr) $v_{max}$ 2936, 2859, 1634, 1602, 1578, 1506, 1436, 1386, 1242, 1216, 1067 cm$^{-1}$; $^1$H NMR (400 MHz, CDCl$_3$) δ 1.69-1.82 (m, 1H, 10α-CH), 2.10-2.19 (m, 1H, 10β-CH), 2.33 (s, 3H, 2-CH$_3$), 2.75-2.84 (m, 1H, 10a-CH), 3.10 (dd, 1H, $^2$J=17.5, $^3$J=6.1 Hz, 11α-CH), 3.20 (dd, 1H, $^2$J=17.5, $^2$J=2.0 Hz, 11β-CH), 3.88 (s, 3H, 3'-OMe), 3.92 (s, 3H, 4'-OMe), 4.02-4.10 (m, 1H, 9α-CH), 4.15-4.23 (m, 1H, 9β-CH), 5.68 (d, 1H, $^3$J=4.2 Hz, 7a-CH), 6.80-6.83 (m, 2H, 2', 6'-H), 6.90 (d, 1H, $^3$J=8.8 Hz, 6-H), 6.93 (d, 1H, $^3$J=8.6 Hz, 5'-H), 8.02 ppm (d, 1H, $^3$J=8.8 Hz, 5-H); $^{13}$C NMR (400 MHz, CDCl$_3$) δ 19.45, 19.53, 27.77, 36.32, 55.90, 55.92, 68.43, 100.85, 106.68, 111.18, 113.68, 115.16, 117.42, 122.80, 123.14, 125.41, 125.73, 148.60, 148.77, 154.99, 156.99, 162.44, 176.57 ppm; MS (CI): m/z 395.3 (MH$^+$, 100). Anal. Calcd for C$_{23}$H$_{22}$O$_6$: C, 70.04; H, 5.62. Found: C, 69.85; H, 5.90.

3-(4-Chlorophenyl)-2-methyl-9,10,10a,11-tetrahydro-4H,7aH-furo[2,3-b]pyrano[2,3-f]chromen-4-one (20i)

Pale yellow solid (60% yield); mp 266-268° C.; IR (KBr) $v_{max}$ 2971, 2903, 1641, 1605, 1582, 1491, 1438, 1399, 1251, 1088, 1068 cm$^{-1}$; $^1$H NMR (400 MHz, CDCl$_3$) δ 1.69-1.83 (m, 1H, 10α-CH), 2.11-2.20 (m, 1H, 10β-CH), 2.32 (s, 3H, 2-CH$_3$), 2.75-2.85 (m, 1H, 10a-CH), 3.10 (dd, 1H, $^2$J=17.4, $^3$J=6.3 Hz, 11α-CH), 3.20 (dd, 1H, $^2$J=17.4, $^2$J=2.1 Hz, 11β-CH), 4.02-4.11 (m, 1H, 9α-CH), 4.16-4.23 (m, 1H, 9β-CH), 5.68 (d, 1H, $^3$J=4.2 Hz, 7a-CH), 6.91 (d, 1H, $^3$J=8.8 Hz, 6-H), 7.19-7.25 (m, 2H, 3', 5'-H), 7.38-7.44 (m, –2', 6'-H), 8.01 ppm (d, 1H, $^3$J=8.8 Hz, 5-H); $^{13}$C NMR (400 MHz, CDCl$_3$) δ 19.38, 19.52, 27.74, 36.28, 68.45, 100.87, 106.75, 115.32, 117.27, 122.34, 125.38, 128.59, 131.65, 131.86, 133.71, 155.01, 157.16, 162.32, 176.10 ppm; MS (CI): m/z 369.1 (MH$^+$, 100), 371.1 (MH$^+$, 29). Anal. Calcd for C$_{21}$H$_{17}$ClO$_4$: C, 68.39; H, 4.65. Found: C, 68.70; H, 4.87.

3-(4-Methoxyphenyl)-11-methyl-6a,7,8,9a-tetrahydro-4H,6H-furo[2,3-b]pyrano[3,2-g]chromen-4-one (25a)

Pale yellow solid (27% yield); mp 155-157° C.; IR (KBr) $v_{max}$ 2963, 2907, 1640, 1606, 1512, 1462, 1289, 1219, 1176, 1056 cm$^{-1}$; $^1$H NMR (400 MHz, CDCl$_3$) δ 1.53-1.67 (m, 1H, 7α-CH), 2.00-2.14 (m, 1H, 7β-CH), 2.33 (s, 3H, 11-CH$_3$), 2.79-2.93 (m, 2H, 6a-CH, 6α-CH), 3.10 (dd, $^2$J=16.4, $^3$J=5.9 Hz, 1H, 6β-CH), 3.83 (s, 3H, 4'-OCH$_3$), 3.88-3.98 (m, 2H, 8-CH$_2$), 5.83 (d, 1H, $^3$J=5.1 Hz, 9a-CH), 6.98 (d, 2H, $^3$J=8.8 Hz, 3', 5'-H), 7.51 (d, 2H, $^3$J=8.8 Hz, 2', 6'-H), 7.91 (s, 1H, 5-H), 8.00 ppm (s, 1H, 2-H); $^{13}$C NMR (100 MHz, CDCl$_3$) δ 8.20, 26.53, 27.97, 37.67, 55.34, 68.33, 102.87, 113.96, 118.62, 120.49, 123.20, 124.19, 124.49, 130.11, 152.27, 154.78, 155.98, 159.49, 176.33 ppm; MS (CI): m/z 365.3 (MH$^+$, 100). Anal. Calcd for C$_{22}$H$_{20}$O$_5$: C, 72.51; H, 5.53. Found: C, 72.80; H, 5.35.

3-(4-Methoxyphenyl)-2,11-methyl-6a,7,8,9a-tetrahydro-4H,6H-furo[2,3-b]pyrano[3,2-g]chromen-4-one (25g)

Pale yellow solid (24% yield); mp 155-157° C.; IR (KBr) $v_{max}$ 2933, 2837, 1635, 1608, 1513, 1462, 1238, 1932 cm$^{-1}$; $^1$H NMR (400 MHz, CDCl$_3$) δ 1.52-1.62 (m, 1H, 7α-CH), 2.02-2.12 (m, 1H, 7β-CH), 2.33, 2.35 (2s, 3H, 3H, 2, 11-CH$_3$), 2.80-2.91 (m, 2H, 6a-CH, 6α-CH), 3.09 (dd, $^2$J=16.0, $^3$J=5.7 Hz, 1H, 6β-CH), 3.84 (s, 3H, 4'-OCH$_3$), 3.88-3.99 (m, 2H, 8-CH$_2$), 5.83 (d, 1H, $^3$J=5.3 Hz, 9a-CH), 6.97 (d, 2H, $^3$J=8.6 Hz, 3', 5'-H), 7.21 (d, 2H, $^3$J=8.6 Hz, 2', 6'-H), 7.82 ppm (s, 1H, 5-H); $^{13}$C NMR (100 MHz, CDCl$_3$) δ 8.24, 19.50, 26.54, 28.03, 37.76, 55.29, 68.32, 102.91, 113.60, 113.88, 117.58, 120.15, 122.38, 123.09, 125.59, 131.59, 154.37, 155.79, 159.00, 162.77, 176.94 ppm; MS (CI): m/z 365.3 (MH$^+$, 100). Anal. Calcd for C$_{22}$H$_{20}$O$_5$: C, 72.51; H, 5.53. Found: C, 72.80; H, 5.35.

General Procedure for the Synthesis of Diels-Alder Adducts 21.

To a solution of 2 mmol of 18 in 10 mL of N,N-dimethylformamide was added 2 mL (22 mmol, 11 eq) of 2H,3,4-dihydropyran. The solution was refluxed for 24-40 h. The solvent and excess 2,3-dihydrofuran were evaporated in vacuo, and the residue was purified by chromatography with 1:50 methanol-dichloromethane to afford 21.

3-(4-Methoxyphenyl)-10,11,11a,12-tetrahydro-4H,7aH,9H-dipyrano[2,3-b:2',3'-f]chromen-4-one (21a)

Pale yellow solid (30% yield); mp 182-183° C.; IR (KBr) $v_{max}$ 2966, 2933, 1636, 1598, 1511, 1437, 1248, 1205, 1178, 1090, 1029 cm$^{-1}$; $^1$H NMR (400 MHz, CDCl$_3$) δ 1.47-1.92 (m, 4H, 10, 11-CH$_2$), 2.24-2.40 (m, 1H, 11a-CH), 2.90 (dd, 1H, $^2$J=17.4 Hz, $^3$J=4.2 Hz, 12α-CH), 3.01 (dd, 1H, $^2$J=17.4, $^3$J=6.1 Hz, 12β-CH), 3.75-3.82 (m, 1H, 9α-CH), 3.85 (s, 3H, 4'-OMe), 3.95-4.09 (m, 1H, 9β-CH), 5.44 (d, 1H, $^3$J=2.0 Hz, 7a-CH), 6.93-7.02 (m, 3H, 6, 3', 5'-H), 7.50 (d, 2H, $^3$J=8.7 Hz, 2', 6'-H), 7.96 (s, 1H, 2-H), 8.10 ppm (d, 1H, $^3$J=8.8 Hz, 5-H); $^{13}$C NMR (400 MHz, CDCl$_3$) δ 23.17, 23.57, 24.02, 30.62, 55.33, 62.58, 96.94, 107.86, 113.94, 115.27, 118.45, 124.19, 124.79, 125.29, 130.13, 151.79, 155.37, 157.15, 159.55, 176.07 ppm; MS (CI): m/z 365.1 (MH$^+$, 100). Anal. Calcd for C$_{22}$H$_{20}$O$_5$: C, 72.51; H, 5.53. Found: C, 72.38; H, 5.67.

3-(3,4-Dimethoxyphenyl)-10,11,11a,12-tetrahydro-4H,7aH,9H-dipyrano[2,3-b:2',3'-f]chromen-4-one (21b)

Pale yellow solid (54% yield); mp 177-178° C.; IR (KBr) $v_{max}$ 3076, 2925, 1642, 1600, 1515, 1436, 1267, 1249, 1139, 1090, 1023 cm$^{-1}$; $^1$H NMR (400 MHz, CDCl$_3$) δ 1.61-1.82 (m, 4H, 10, 11-CH$_2$), 2.27-2.37 (m, 1H, 11a-CH), 2.91 (dd, 1H, $^2$J=17.3, $^3$J=4.1 Hz, 12α-CH), 2.99 (dd, 1H, $^2$J=17.3, $^3$J=6.1 Hz, 12β-CH), 3.76-3.83 (m, 1H, 9α-CH), 3.92 (s, 3H, 3'-OMe), 3.93 (s, 3H, 4'-OMe), 4.00-4.08 (m, 1H, 9β-CH), 5.45 (d, 1H, $^3$J=2.0 Hz, 7a-CH), 6.93 (d, 1H, $^3$J=8.3 Hz, 5'-H), 6.98 (d, 1H, $^3$J=8.9 Hz, 6-H), 7.04 (dd, 1H, $^3$J=8.3, $^4$J=2.0 Hz, 6'-H), 7.22 (d, 1H, $^4$J=2.0 Hz, 2'-H), 7.99 (s, 1H, 2-H), 8.09 ppm (d, 1H, $^3$J=8.9 Hz, 5-H); $^{13}$C NMR (400 MHz, CDCl$_3$) δ 23.15, 23.56, 24.05, 30.64, 55.96, 55.98, 62.61, 96.97, 107.89, 111.16, 112.55, 115.34, 118.46, 121.02, 124.67, 124.83, 125.26, 148.76, 149.10, 151.96, 155.35, 157.22, 176.06 ppm; MS (CI): m/z 395.3 (MH$^+$, 100). Anal. Calcd for $C_{23}H_{22}O_6$: C, 70.04; H, 5.62. Found: C, 70.27; H, 5.90.

3-(1,3-Benzodioxol-5-yl)-10,11,11a,12-tetrahydro-4H,7aH,9H-dipyrano[2,3-b:2',3'-f]chromen-4-one (21c)

Pale yellow solid (25% yield); mp 179-181° C.; IR (KBr) $\nu_{max}$ 2925, 1637, 1599, 1434, 1247, 1142, 1033 cm$^{-1}$; $^1$H NMR (400 MHz, CDCl$_3$) δ 1.68-1.84 (m, 4H, 10, 11-CH$_2$), 2.25-2.37 (m, 1H, 11a-CH), 2.83-3.08 (m, 2H, 12α, 12β-CH), 3.75-3.85 (m, 1H, 9α-CH), 4.00-4.09 (m, 1H, 9β-CH), 5.44 (d, 1H, $^3J$=2.4 Hz, 7a-CH), 6.00 (s, 2H, OCH$_2$O), 6.88 (d, 1H, $^3J$=8.0 Hz, 7'-H), 6.95-7.01 (m, 2H, 6, 6'-H), 7.10 (d, 1H, $^3J$=1.7 Hz, 4'-H), 7.95 (s, 1H, 2-H), 8.09 ppm (d, 1H, $^3J$=8.8 Hz, 5-H); $^{13}$C NMR (400 MHz, CDCl$_3$) δ 23.19, 23.58, 24.05, 30.63, 62.58, 96.91, 101.11, 107.82, 108.31, 109.71, 115.29, 118.30, 122.31, 124.86, 125.23, 125.56, 147.53, 147.55, 151.88, 155.25, 157.13, 175.82 ppm; MS (CI): m/z 379.2 (MH$^+$, 100). Anal. Calcd for $C_{22}H_{18}O_6$: C, 69.84; H, 4.79. Found: C, 70.07; H, 4.61.

3-(2,3-Dihydro-1,4-benzodioxin-6-yl)-10,11,11a,12-tetrahydro-4H,7aH,9H-dipyrano[2,3-b:2',3'-f]chromen-4-one (21d)

Pale yellow solid (36% yield); mp 160-162° C.; IR (KBr) $\nu_{max}$ 2943, 2924, 2860, 1635, 1599, 1507, 1436, 1303, 1287, 1249, 1091 cm$^{-1}$; $^1$H NMR (400 MHz, CDCl$_3$) δ 1.67-1.82 (m, 4H, 10, 11-CH$_2$), 2.27-2.35 (m, 1H, 11a-CH), 2.91 (dd, 1H, $^2J$=17.3, $^3J$=4.1 Hz, 12α-CH), 2.99 (dd, 1H, $^2J$=17.3, $^3J$=6.1 Hz, 12β-CH), 3.75-3.83 (m, 1H, 9α-CH), 4.00-4.09 (m, 1H, 9β-CH), 4.27-4.31 (m, 4H, OCH$_2$CH$_2$O), 5.44 (d, 1H, $^3J$=2.4 Hz, 7a-CH), 6.93 (d, 1H, $^3J$=8.3 Hz, 8'-H), 6.97 (d, 1H, $^3J$=8.9 Hz, 6-H), 7.03 (dd, 1H, $^3J$=8.3, $^4J$=2.1 Hz, 7'-H), 7.10 (d, 1H, $^4J$=2.1 Hz, 5'-H), 7.94 (s, 1H, 2-H), 8.09 ppm (d, 1H, $^3J$=8.9 Hz, 5-H); $^{13}$C NMR (400 MHz, CDCl$_3$) δ 23.19, 23.58, 24.01, 30.63, 62.56, 64.32, 64.46, 96.94, 107.85, 115.27, 117.28, 117.96, 118.45, 122.18, 124.67, 125.12, 125.32, 143.42, 143.68, 151.93, 155.33, 157.17, 175.90 ppm; MS (CI): m/z 393.2 (MH$^+$, 100). Anal. Calcd for $C_{23}H_{20}O_6$: C, 70.40; H, 5.14. Found: C, 70.15; H, 5.40.

3-(4-Chlorophenyl)-10,11,11a,12-tetrahydro-4H,7aH,9H-dipyrano[2,3-b:2',3'-f]chromen-4-one (21e)

Pale yellow solid (19% yield); mp 195-197° C.; IR (KBr) $\nu_{max}$ 2930, 1643, 1597, 1437, 1256, 1206, 1094, 826 cm$^{-1}$; $^1$H NMR (400 MHz, CDCl$_3$) δ 1.67-1.84 (m, 4H, 10, 11-CH$_2$), 2.28-2.38 (m, 1H, 11a-CH), 2.85-3.07 (m, 2H, 12α, 12β-CH), 3.76-3.85 (m, 1H, 9α-CH), 3.99-4.11 (m, 1H, 9β-CH), 5.45 (d, 1H, $^3J$=2.4 Hz, 7a-CH), 6.99 (d, 1H, $^3J$=8.8 Hz, 6-H), 7.42 (d, 2H, $^3J$=8.7 Hz, 3', 5'-H), 7.52 (d, 2H, $^3J$=8.7 Hz, 2', 6'-H), 7.99 (s, 1H, 2-H), 8.09 ppm (d, 1H, $^3J$=8.9 Hz, 5-H); $^{13}$C NMR (400 MHz, CDCl$_3$) δ 23.20, 23.59, 24.05, 30.61, 62.60, 96.93, 107.89, 115.47, 118.33, 124.13, 125.25, 128.60, 130.16, 130.32, 134.06, 152.16, 155.28, 157.28, 175.27 ppm; MS (CI): m/z 369.2 (MH$^+$, 100), 371.2 (MH$^+$, 25). Anal. Calcd for $C_{21}H_{17}ClO_4$: C, 68.39; H, 4.65. Found: C, 68.17; H, 4.43.

2-Methyl-3-phenyl-10,11,11a,12-tetrahydro-4H,7aH,9H-dipyrano[2,3-b:2',3'-f]chromen-4-one (21f)

Pale yellow solid (33% yield); mp 165-167° C.; IR (KBr) $\nu_{max}$ 2927, 1626, 1600, 1440, 1400, 1255, 1139, 1090 cm$^{-1}$; $^1$H NMR (400 MHz, CDCl$_3$) δ 1.66-1.81 (m, 4H, 10, 11-CH$_2$), 2.32 (s, 4H, 2-CH$_3$, 11a-CH), 2.86-3.08 (m, 2H, 12α, 12β-CH), 3.75-3.86 (m, 1H, 9α-CH), 4.01-4.11 (m, 1H, 9β-CH), 5.45 (d, 1H, $^3J$=2.4 Hz, 7a-CH), 6.94 (d, 1H, $^3J$=8.8 Hz, 6-H), 7.28-7.32 (m, 2H, 2', 6'-H), 7.36 (t, 1H, $^3J$=7.3 Hz, 4'-H), 7.44 (t, 2H, $^3J$=7.3 Hz, 3', 5'-H), 8.02 ppm (d, 1H, $^3J$=8.9 Hz, 5-H); $^{13}$C NMR (400 MHz, CDCl$_3$) δ 19.43, 23.24, 23.62, 24.09, 30.72, 62.58, 96.86, 107.44, 114.77, 117.37, 123.30, 125.15, 127.59, 128.25, 130.36, 133.16, 154.87, 156.87, 162.15, 176.26 ppm; MS (CI): m/z 349.2 (MH$^+$, 100). Anal. Calcd for $C_{22}H_{20}O_4$: C, 75.84; H, 5.79. Found: C, 76.01; H, 5.95.

3-(4-Methoxyphenyl)-2-methyl-10,11,11a,12-tetrahydro-4H,7aH,9H-dipyrano[2,3-b:2',3'-f]chromen-4-one (21g)

Pale yellow solid (34% yield); mp 199-200° C.; IR (KBr) $\nu_{max}$ 2931, 2901, 1637, 1606, 1510, 1440, 1397, 1255, 1243, 1136, 1091, 1030 cm$^{-1}$; $^1$H NMR (400 MHz, CDCl$_3$) δ 1.61-1.82 (m, 4H, 10, 11-CH$_2$), 2.28-2.35 (m, 4H, 2-CH$_3$, 11a-CH), 2.92 (dd, 1H, $^2J$=17.3, $^3J$=4.2 Hz, 12α-CH), 3.00 (dd, 1H, $^2J$=17.3, $^3J$=6.3 Hz, 12β-CH), 3.76-3.83 (m, 1H, 9α-CH), 3.85 (s, 3H, 4'-OMe), 4.00-4.10 (m, 1H, 9β-CH), 5.44 (d, 1H, $^3J$=2.2 Hz, 7a-CH), 6.93 (d, 1H, $^3J$=8.8 Hz, 6-H), 6.97 (d, 2H, $^3J$=8.7 Hz, 3', 5'-H), 7.21 (d, 2H, $^3J$=8.7 Hz, 2', 6'-H), 8.01 ppm (d, 1H, $^3J$=8.8 Hz, 5-H); $^{13}$C NMR (400 MHz, CDCl$_3$) δ 19.41, 23.18, 23.58, 24.06, 30.69, 55.28, 62.59, 96.90, 107.48, 113.84, 114.76, 117.38, 122.88, 125.19, 125.32, 131.55, 154.94, 156.91, 159.02, 162.25, 176.63 ppm; MS (CI): m/z 379.3 (MH$^+$, 100). Anal. Calcd for $C_{23}H_{22}O_5$: C, 73.00; H, 5.86. Found: C, 73.18; H, 6.02.

3-(3,4-Dimethoxyphenyl)-2-methyl-10,11,11a,12-tetrahydro-4H,7aH,9H-dipyrano[2,3-b:2',3'-f]chromen-4-one (21h)

Pale yellow solid (15% yield); mp 209-210° C.; IR (KBr) $\nu_{max}$ 2934, 1636, 1581, 1513, 1438, 1394, 1258, 1138 cm$^{-1}$; $^1$H NMR (400 MHz, CDCl$_3$) δ 1.56-1.82 (m, 4H, 10, 11-CH$_2$), 2.27-2.35 (m, 4H, 2-CH$_3$, 11a-CH), 2.98 (dd, 1H, $^2J$=17.2, $^3J$=4.4 Hz, 12α-CH), 3.00 (dd, 1H, $^2J$=17.2, $^3J$=6.3 Hz, 12β-CH), 3.75-3.83 (m, 1H, 9α-CH), 3.88 (s, 3H, 3'-OMe), 3.92 (s, 3H, 4'-OMe), 4.00-4.10 (m, 1H, 9β-CH), 5.44 (d, 1H, $^3J$=2.4 Hz, 7a-CH), 6.79-6.83 (m, 2H, 2', 6'-H), 6.91-6.95 (m, 2H, 6, 5'-H), 8.02 ppm (d, 1H, $^3J$=8.8 Hz, 5-H); $^{13}$C NMR (400 MHz, CDCl$_3$) δ 19.45, 23.17, 23.57, 24.08, 30.69, 55.90, 55.91, 62.61, 96.93, 107.51, 111.17, 113.68, 114.86, 117.37, 122.81, 123.12, 125.19, 125.76, 148.58, 148.76, 154.97, 156.99, 162.51, 176.68 ppm; MS (CI): m/z 409.2 (MH$^+$, 100). Anal. Calcd for $C_{24}H_{24}O_6$: C, 70.58; H, 5.92. Found: C, 70.69; H, 6.17.

3-(4-Chlorophenyl)-2-methyl-10,11,11a,12-tetrahydro-4H,7aH,9H-dipyrano[2,3-b:2',3'-f]chromen-4-one (21i)

Pale yellow solid (15% yield); mp 205-206° C.; IR (KBr) $\nu_{max}$ 2927, 1635, 1605, 1439, 1398, 1257, 1139, 1094, 895 cm$^{-1}$; $^1$H NMR (400 MHz, CDCl$_3$) δ 1.82-1.64 (m, 4H, 10, 11-CH$_2$), 2.28-2.37 (m, 4H, 2-CH$_3$, 11a-CH), 2.84-3.07 (m, 2H, 12α, 12β-CH), 3.75-3.84 (m, 1H, 9α-CH), 4.00-4.10 (m, 1H, 9β-CH), 5.44 (d, 1H, $^3J$=2.5 Hz, 7a-CH), 6.95 (d, 1H, $^3J$=8.8 Hz, 6-H), 7.20-7.25 (m, 2H, 2', 6'-H), 7.38-7.43 (m, 2H, 3', 5'-H), 8.01 ppm (d, 1H, $^3J$=8.8 Hz, 5-H); $^{13}$C NMR (400 MHz, CDCl$_3$) δ 19.38, 23.12, 23.51, 24.03, 30.60, 62.59, 96.90, 107.55, 115.03, 117.15, 122.27, 125.16, 128.57, 131.59, 131.83, 133.67, 154.96, 157.15, 162.44, 176.20 ppm; MS (CI): m/z 383.2 (MH$^+$, 100), 385.2 (MH$^+$, 25). Anal. Calcd for $C_{22}H_{19}ClO_3$: C, 72.03; H, 5.22. Found: C, 72.31; H, 5.43.

General Procedure for the Synthesis of Diels-Alder Adducts 22 and 26.

To a solution of 1 mmol of 18 or 19 was added 1.25 mmol (1.25 eq) of 3-(N,N-dimethylamino)-5,5-dimethylcyclohex-2-en-1-one in 10 mL of N,N-dimethylformamide. The solution was refluxed for 4 h. The mixture was diluted with 20 mL of methanol, and the precipitate was collected by filtration and re-crystallized from N,N-dimethylformamide-methanol to afford 22 or 26.

3-(4-Methoxyphenyl)-9,9-dimethyl-8,9,10,12-tetrahydro-4H,11H-pyrano[2,3-a]xanthene-4,11-dione (22a)

Beige solid (92% yield); mp 223-225° C.; IR (KBr) $v_{max}$ 2949, 1647, 1606, 1511, 1438, 1237, 1032 cm$^{-1}$; $^1$H NMR (400 MHz, DMSO-d$_6$) δ 1.10 (s, 6H, 9-CH$_3$), 2.33 (s, 2H, 10-CH$_2$), 2.53 (2, 2H, 8-CH$_2$), 3.52 (s, 2H, 12-CH$_2$), 3.81 (s, 3H, 4'-OCH$_3$), 7.01 (d, 2H, $^3$J=8.6, 3', 5'-H), 7.18 (d, 1H, д, $^3$J=8.8, 6-H), 7.54 (d, 2H, $^3$J=8.6, 2', 6'-H), 8.00 (d, 2H, $^3$J=8.8, 5-H), 8.50 ppm (s, 1H, 2-H); $^{13}$C NMR (125 MHz, CDCl$_3$ and DMSO-d$_6$ 1:1) δ 16.01, 27.89, 31.67, 40.57, 50.07, 54.80, 107.61, 109.39, 113.36, 113.84, 120.34, 123.22, 124.36, 124.84, 129.51, 151.86, 152.47, 153.99, 159.01, 163.63, 174.96, 196.87 ppm; MS (CI): m/z 403.2 (MH$^+$, 100). Anal. Calcd for $C_{25}H_{22}O_5$: C, 74.61; H, 5.51. Found: C, 74.47; H, 5.27.

3-(3,4-Dimethoxyphenyl)-9,9-dimethyl-8,9,10,12-tetrahydro-4H,11H-pyrano[2,3-a]xanthene-4,11-dione (22b)

Beige solid (75% yield); mp 196-198° C.; IR (KBr) $v_{max}$ 2955, 1654, 1640, 1516, 1440, 1261, 1237, 1195 cm$^{-1}$; $^1$H NMR (400 MHz, CDCl$_3$) δ 1.17 (s, 6H, 9-CH$_3$), 2.39 (s, 2H, 10-CH$_2$), 2.50 (s, 2H, 8-CH$_2$), 3.65 (s, 2H, 12-CH$_2$), 3.93, 3.94 (2s, 6H, 3', 4'-OCH$_3$), 6.94 (d, 1H, $^3$J=8.3 Hz, 5'-H), 7.02-7.10 (m, 2H, 6, 6'-H), 7.21 (d, 1H, $^4$J=1.8 Hz, 2'-H), 8.04 (s, 1H, 2-H), 8.15 ppm (d, 1H, $^3$J=8.3 Hz, 5-H); $^{13}$C NMR (400 MHz, CDCl$_3$) δ 16.51, 28.42, 32.20, 41.17, 50.60, 55.94, 55.96, 108.31, 109.99, 111.18, 112.39, 114.45, 121.02, 121.07, 124.17, 125.20, 125.60, 148.80, 149.24, 152.51, 153.12, 154.62, 164.28, 175.76, 197.69 ppm; MS (CI): m/z 433.3 (MH$^+$, 100). Anal. Calcd for $C_{26}H_{24}O_6$: C, 72.21; H, 5.59. Found: C, 72.49; H, 5.22.

3-(1,3-Benzodioxol-5-yl)-9,9-dimethyl-8,9,10,12-tetrahydro-4H,11H-pyrano[2,3-a]xanthene-4,11-dione (22c)

Beige solid (80% yield); mp 258-260° C.; IR (KBr) $v_{max}$ 2950, 2897, 1649, 1599, 1429, 1240, 1194, 1037 cm$^{-1}$; $^1$H NMR (400 MHz, CDCl$_3$) δ 1.17 (s, 6H, 9-CH$_3$), 2.39 (s, 2H, 10-CH$_2$), 2.50 (s, 2H, 8-CH$_2$), 3.64 (s, 2H, c, 12-CH$_2$), 6.00 (s, 2H, OCH$_2$O), 6.88 (d, 1H, $^3$J=8.0 Hz, 5'-H), 6.99 (dd, 1H, $^4$J=1.7 Hz, $^3$J=8.0 Hz, 6'-H), 7.05 (d, 1H, $^3$J=8.8 Hz, 6-H), 7.10 (d, 1H, $^4$J=1.7 Hz, 2'-H), 8.00 (s, 1H, 2-H), 8.15 ppm (d, 1H, $^3$J=8.8 Hz, 5-H); $^{13}$C NMR (100 MHz, CDCl$_3$) δ 16.52, 28.43, 32.21, 41.19, 50.61, 101.22, 108.33, 108.45, 109.71, 110.01, 114.46, 120.99, 122.42, 125.23, 125.32, 125.69, 147.74, 147.81, 152.49, 153.15, 154.65, 164.28, 175.62, 197.69 ppm; MS (CI): m/z 417.3 (MH$^+$, 100). Anal. Calcd for $C_{25}H_{20}O_6$: C, 72.11; H, 4.84. Found: C, 72.29; H, 5.11.

2,9,9-trimethyl-3-phenyl-8,9,10,12-tetrahydro-4H,11H-pyrano[2,3-a]xanthene-4,11-dione (22f)

Beige solid (84% yield); mp 265-266° C.; IR (KBr) $v_{max}$ 3047, 2947, 2885, 1646, 1590, 1390, 1235, 1215, 700 cm$^{-1}$; $^1$H NMR (400 MHz, CDCl$_3$) δ 1.17 (s, 6H, 9-CH$_3$), 2.35 (s, 3H, 2-CH$_3$), 2.40 (s, 2H, 10-CH$_2$), 2.51 (s, 2H, 8-CH$_2$), 3.66 (s, 2H, 12-CH$_2$), 7.01 (d, 1H, $^3$J=8.8 Hz, 6-H), 7.26-7.30 (m, 2H, 2', 6'-H), 7.35-7.40 (m, 1H, 4'-H), 7.41-7.47 (m, 2H, 3', 5'-H), 8.08 ppm (d, 1H, $^3$J=8.8 Hz, 5-H); $^{13}$C NMR (100 MHz, CDCl$_3$) δ 16.48, 19.55, 28.42, 32.20, 41.22, 50.64, 108.34, 109.56, 113.99, 120.04, 123.73, 125.56, 127.85, 128.41, 130.34, 132.82, 152.94, 154.29, 163.30, 164.46, 176.08, 197.89 ppm; MS (CI): m/z 387.3 (MH$^+$, 100). Anal. Calcd for $C_{25}H_{22}O_4$: C, 77.70; H, 5.74. Found: C, 77.92; H, 5.88.

3-(4-Methoxyphenyl)-2,9,9-trimethyl-8,9,10,12-tetrahydro 4H,11H-pyrano[2,3-a]xanthene-4,11-dione (22g)

Beige solid (90% yield); mp 236-237° C.; IR (KBr) $v_{max}$ 2958, 2890, 1653, 1586, 1515, 1440, 1393, 1239, 1174, 1026 cm$^{-1}$; $^1$H NMR (400 MHz, CDCl$_3$) δ 1.14 (s, 6H, 9-CH$_3$), 2.32 (s, 3H, 2-CH$_3$), 2.36 (s, 2H, 10-CH$_2$), 2.47 (s, 2H, 8-CH$_2$), 3.62 (s, 2H, 12-CH$_2$), 3.82 (s, 3H, 4'-OCH$_3$), 6.92-6.99 (m, 3H, 6, 3', 5'-H), 7.15-7.21 (m, 2H, 2', 6'-H), 8.04 ppm (d, 1H, $^3$J=8.8 Hz, 5-H); $^{13}$C NMR (100 MHz, CDCl$_3$) δ 16.47, 19.56, 28.42, 32.19, 41.23, 50.65, 55.28, 108.36, 109.52, 113.92, 113.93, 120.02, 123.28, 124.91, 125.56, 131.50, 152.90, 154.26, 159.17, 163.25, 164.46, 176.30, 197.86 ppm; MS (CI): m/z 417.3 (MH$^+$, 100). Anal. Calcd for $C_{26}H_{24}O_5$: C, 74.98; H, 5.81. Found: C, 74.70; H, 6.10.

3-(4-Methoxyphenyl)-9,9-trimethyl-6,8,9,10-tetrahydro-4H,7H-pyrano[3,2-b]xanthene-4,7-dione (26a)

Beige solid (80% yield); mp 230-232° C.; IR (KBr) $v_{max}$ 3079, 2958, 2835, 1645, 1612, 1514, 1463, 1391, 1296, 1220, 1179 cm$^{-1}$; $^1$H NMR (400 MHz, CDCl$_3$) δ 1.16 (s, 6H, 9-CH$_3$), 2.35 (s, 2H, 8-CH$_2$), 2.39 (s, 3H, 12-CH$_3$), 2.52 (s, 2H, 10-CH$_2$), 3.62 (s, 2H, 6-CH$_2$), 3.84 (s, 3H, 4'-OCH$_3$), 6.97 (d, 2H, $^3$J=8.8 Hz, 3', 5'-H), 7.50 (d, 2H, $^3$J=8.8 Hz, 2', 6'-H), 7.96 (s, 1H, 5-H), 8.00 ppm (s, 1H, 2-H); $^{13}$C NMR (100 MHz, CDCl$_3$) δ 8.32, 20.97, 28.45, 32.20, 41.29, 50.62, 55.34, 109.16, 113.99, 114.18, 118.85, 120.88, 124.05, 124.16, 124.49, 130.05, 151.43, 152.48, 153.96, 159.62, 163.91, 175.92, 197.56 ppm; MS (CI): m/z 417.3 (MH$^+$, 100). Anal. Calcd for $C_{26}H_{14}O_5$: C, 74.98; H, 5.81. Found: C, 75.22; H, 5.64.

3-(4-Methoxyphenyl)-2,9,9,12-tetramethyl-6,8,9,10-tetrahydro-4H,7H-pyrano[3,2-b]xanthene-4,7-dione (26g)

Beige solid (72% yield); mp 270-272° C.; IR (KBr) $v_{max}$ 2954, 2878, 1642, 1609, 1395, 1238, 1220, 1142 cm$^{-1}$; $^1$H NMR (400 MHz, CDCl$_3$) δ 1.16 (s, 6H, 9-CH$_3$), 2.34 (s, 3H, 2-CH$_3$), 2.36 (s, 2H, 8-CH$_2$), 2.40 (s, 3H, 12-CH$_3$), 2.52 (2H, 10-CH$_2$), 3.61 (s, 2H, 6-CH$_2$), 3.85 (s, 3H, 4'-OCH$_3$), 6.97 (d, 2H, $^3$J=8.7 Hz, 3', 5'-H), 7.20 (d, 2H, $^3$J=8.7 Hz, 2', 6'-H), 7.89 ppm (s, 1H, 5-H); $^{13}$C NMR (100 MHz, CDCl$_3$) δ 8.33, 19.54, 20.95, 28.47, 32.20, 41.33, 50.63, 55.29, 109.19, 113.70, 113.91, 118.35, 119.84, 122.75, 124.08, 125.16, 131.54, 151.26, 153.58, 159.11, 163.11, 163.96, 176.53, 197.61 ppm; MS (CI): m/z 431.1 (MH$^+$, 100). Anal. Calcd for C$_{27}$H$_{26}$O$_5$: C, 75.33; H, 6.09. Found: C, 75.52; H, 5.87.

General Procedure for the Synthesis of Diels-Alder Adducts 23 and 24.

To a solution of 2 mmol of 18 in 10 mL of N,N-dimethylformamide was added 2.2 mmol (1.1 eq) of 1-morpholinocyclopentene or 1-morpholinocyclohexene. The mixture was heated at 154° C. for 4 h. The solvent was evaporated in vacuo, and residue was chromatographed using 1:50 methanol-dichloromethane to afford 23 or 24.

7-Hydroxy-3-(4-methoxyphenyl)-2-methyl-8-[(2-oxocyclopentyl)methyl]-4H-chromen-4-one (23g)

Pale yellow solid (58% yield); mp 210-211° C.; IR (KBr) ν$_{max}$ 2960, 1735, 1631, 1580, 1512, 1436, 1291, 1244 cm$^{-1}$; $^1$H NMR (400 MHz, CDCl$_3$) δ 1.62-2.25 (m, 4H, 4", 5"-CH$_2$), 2.33 (s, 3H, 2-CH$_3$), 2.38-2.63 (m, 2H, 3"-CH$_2$), 3.01-3.17 (m, 2H, 8-CH$_2$), 3.37-3.74 (m, 1H, 1"-H), 3.84 (s, 3H, 4'-OCH$_3$), 6.91-7.00 (m, 3H, 6, 3', 5'-H), 7.21 (d, 2H, $^3$J=8.6 Hz, 2', 6'-H), 7.99 ppm (d, 1H, $^3$J=8.7 Hz, 5-H); $^{13}$C NMR (125 MHz, DMSO-d$_6$) δ 19.15, 20.05, 22.40, 28.91, 37.40, 48.03, 55.04, 113.25, 113.43, 113.69, 115.56, 121.25, 124.27, 125.31, 131.67, 155.07, 158.46, 159.94, 162.29, 175.36, 219.25 ppm; MS (CI): m/z 379.1 (MH$^+$, 100). Anal. Calcd for C$_{23}$H$_{22}$O$_5$: C, 73.00; H, 5.86. Found: C, 73.26; H, 5.62.

3-(3,4-Dimethoxyphenyl)-7-hydroxy-2-methyl-8-[(2-oxocyclopentyl)methyl]-4H-chromen-4-one (23h)

Pale yellow solid (53% yield); mp 88-90° C.; IR (KBr) ν$_{max}$ 2924, 1736, 1633, 1515, 1440, 1265 cm$^{-1}$; $^1$H NMR (400 MHz, DMSO-d$_6$) δ 1.51-2.07 (m, 4H, 4", 5"-CH$_2$), 2.27 (s, 3H, 2-CH$_3$), 2.66-3.16 (m, 4H, 8, 3"-CH$_2$), 3.36-3.60 (m, 1H, 1"-H), 3.74, 3.79 (2s, 6H, 3', 4'-OCH$_3$), 6.74-6.88 (m, 2H, 2', 6'-H), 6.93-7.03 (m, 2H, 6, 5'-H), 7.76 (d, 1H, $^3$J=8.7 Hz, 5-H), 10.64 ppm (s, 1H, 7-OH); $^{13}$C NMR (125 MHz, DMSO-d$_6$) δ 19.63, 20.47, 29.33, 37.83, 48.43, 55.93, 55.97, 111.89, 113.68, 114.12, 114.80, 116.05, 122.01, 123.24, 124.70, 126.17, 148.54, 148.68, 155.50, 160.34, 162.85, 175.75, 219.65 ppm; MS (CI): m/z 409.2 (MH$^+$, 100). Anal. Calcd for C$_{24}$H$_{24}$O$_6$: C, 70.58; H, 5.92. Found: C, 70.28; H, 6.18.

7a-Hydroxy-3-(4-methoxyphenyl)-8,9,10,11,11a,12-hexahydro-4H,7aH-pyrano[2,3-a]xanthen-4-one (24a)

Pale yellow solid (91% yield); mp 222-223° C.; IR (KBr) ν$_{max}$ 2987, 1613, 1513, 1439, 1251, 1030 cm$^{-1}$; $^1$H NMR (400 MHz, CDCl$_3$) δ 1.30-2.18 (m, 9H, 8, 9, 10, 11-CH$_2$, 11a-CH), 2.35-3.26 (m, 2H, 12-CH$_2$), 3.85 (s, 3H, 4'-OCH$_3$), 6.81-6.89 (m, 1H, 6-H), 6.98 (d, 2H, $^3$J=8.6 Hz, 3', 5'-H), 7.51 (d, 2H, $^3$J=8.6 Hz, 2', 6'-H), 7.96 (s, 1H, 2-H), 8.02-8.09 ppm (m, 1H, 5-H); $^{13}$C NMR (125 MHz, DMSO-d$_6$) δ 21.82 (21.73), 22.82 (23.00), 24.93 (24.30), 29.11 (28.59), 36.33 (35.45), 37.51 (37.28), 55.13, 98.10 (97.70), 111.20 (108.97), 113.58, 115.63 (115.65), 117.11 (117.33), 123.13 (123.18), 123.84, 124.16, 130.06 (130.08), 153.15, 154.26 (154.95), 156.84 (156.37), 158.96, 174.88 (174.86) ppm; MS (CI): m/z 349.2 (MH$^+$, 100). Anal. Calcd for C$_{23}$H$_{22}$O$_5$: C, 73.00; H, 5.86. Found: C, 72.71; H, 5.98.

3-(3,4-Dimethoxyphenyl)-7a-hydroxy-8,9,10,11,11a,12-hexahydro-4H,7aH-pyrano[2,3-a]xanthen-4-one (24b)

Pale yellow solid (85% yield); mp 214-216° C.; IR (KBr) ν$_{max}$ 2930, 1629, 1612, 1516, 1439, 1263, 1143, 1027 cm$^{-1}$; $^1$H NMR (400 MHz, DMSO-d$_6$) δ 1.40-2.62 (m, 9H, 8, 9, 10, 11-CH$_2$, 11a-CH), 2.70-3.60 (m, 2H, 12-CH$_2$), 3.75 (s, 6H, 3', 4'-OCH$_3$), 6.84-6.99, 7.07-7.19 (2m, 4H, 6, 2', 5', 6'-H), 7.81-7.87 (m, 1H, 5-H), 8.42, 8.43 ppm (2s, 1H, 2-H); $^{13}$C NMR (125 MHz, DMSO-d$_6$) δ 22.22 (22.13), 23.25 (23.42), 25.35 (24.73), 29.54 (29.02), 36.76 (35.87), 37.94 (37.71), 55.96, 55.96, 98.54 (98.13), 109.39 (109.30), 111.95 (111.62), 113.17, 116.10 (116.07), 117.56 (117.78), 121.63 (121.66), 123.63 (123.63), 124.28, 124.90 (124.91), 148.68, 149.03, 153.79, 154.63 (155.32), 157.27 (156.79), 175.28 (175.26) ppm; MS (CI): m/z 409.2 (MH$^+$, 100). Anal. Calcd for C$_{24}$H$_{24}$O$_6$: C, 70.58; H, 5.92. Found: C, 70.31; H, 6.21.

3-(1,3-Benzodioxol-5-yl)-7a-hydroxy-8,9,10,11,11a,12-hexahydro-4H,7aH-pyrano[2,3-a]xanthen-4-one (24c)

Pale yellow solid (76% yield); mp 197-197° C.; IR (KBr) ν$_{max}$ 2937, 1630, 1587, 1435, 1251, 1027 cm$^{-1}$; $^1$H NMR (400 MHz, DMSO-d$_6$) δ 1.23-2.62 (m, 9H, 8, 9, 10, 11-CH$_2$, 11a-CH), 2.70-3.60 (m, 2H, 12-CH$_2$), 6.05 (s, 2H, OCH$_2$O), 6.88-7.18 (2m, 4H, 6, 2', 5', 6'-H), 7.81-7.99 (m, 1H, 5-H), 8.41, 8.45 ppm (2s, 1H, 2-H); $^{13}$C NMR (125 MHz, DMSO-d$_6$) δ 22.24 (22.14), 23.24 (23.42), 25.35 (24.72), 29.53 (29.02), 36.76 (35.88), 37.95 (37.70), 98.56 (98.15), 101.45, 108.51, 109.83 (109.86), 111.65, 116.13 (116.10), 117.49 (117.72), 122.81 (122.84), 123.58 (123.63), 124.29, 126.11 (126.13), 147.34, 147.41, 153.86 (153.64), 154.64 (155.33), 157.32 (156.86), 175.16 (175.15) ppm; MS (CI): m/z 393.2 (MH$^+$, 100). Anal. Calcd for C$_{23}$H$_{20}$O$_6$: C, 70.40; H, 5.14. Found: C, 70.14; H, 4.85.

7a-Hydroxy-3-(4-methoxyphenyl)-2-methyl-8,9,10,11,11a,12-hexahydro-4H,7aH-pyrano[2,3-a]xanthen-4-one (24g)

Pale yellow solid (69% yield); mp 212-213° C.; IR (KBr) ν$_{max}$ 2924, 1632, 1608, 1514, 1435, 1251, 1177 cm$^{-1}$; $^1$H NMR (400 MHz, CDCl$_3$) δ 1.57-2.17 (m, 9H, 8, 9, 10, 11-CH$_2$, 11a-CH), 2.33 (s, 3H, 2-CH$_3$), 2.54-3.27 (m, 2H, 12-CH$_2$), 3.85 (s, 3H, 4'-OCH$_3$), 6.70-6.81 (m, 1H, 6-H), 6.97 (d, 2H, $^3$J=8.5 Hz, 3', 5'-H), 7.21 (d, 2H, $^3$J=8.5 Hz, 2', 6'-H), 7.87-7.97 ppm (m, 1H, 5-H); $^{13}$C NMR (400 MHz, CDCl$_3$) δ 19.43 (19.44), 22.12 (21.97), 23.09 (23.34), 25.51 (24.92), 29.44 (29.13), 36.64 (38.54), 37.80 (37.85), 55.29, 97.93 (97.76), 110.68 (108.50), 113.85, 115.24 (115.21), 116.93 (117.14), 122.74 (122.77), 124.61 (124.70), 125.50 (125.51), 131.61, 154.48 (155.18), 155.81 (156.39), 159.02, 162.51 (162.51), 177.10 (177.07) ppm; MS (CI): m/z 393.2 (MH$^+$, 100). Anal. Calcd for C$_{24}$H$_{24}$O$_5$: C, 73.45; H, 6.16. Found: C, 73.18; H, 6.42.

3-(3,4-Dimethoxyphenyl)-7a-hydroxy-2-methyl-8,9,10,11,11a,12-hexahydro-4H,7aH-pyrano[2,3-a]xanthen-4-one (24h)

Pale yellow solid (51% yield); mp 193-194; IR (KBr) ν$_{max}$ 2938, 1631, 1610, 1577, 1514, 1437, 1264, 1028 cm$^{-1}$;

¹H NMR (400 MHz, CDCl₃) δ 1.30-2.16 (m, 9H, 8, 9, 10, 11-CH₂, 11a-CH), 2.34 (s, 3H, 2-CH₃), 2.53-3.28 (m, 2H, 12-CH₂), 3.88, 3.92 (2s, 6H, 3', 4'-OCH₃), 6.62-6.99 (m, 1H, 6-H), 6.78-6.86, 6.90-6.96 (2m, 3H, 2', 5', 6'-H), 7.84-7.92 ppm (m, 1H, 5-H); ¹³C NMR (125 MHz, DMSO-d₆) δ 19.19 (19.21), 21.76 (21.69), 22.80 (22.99), 24.96 (24.32), 29.10 (28.59), 36.36 (35.46), 37.57 (37.31), 55.47, 55.50, 97.97 (97.58), 110.87 (108.64), 111.41, 114.31, 115.20 (115.17), 116.05 (116.27), 122.02 (122.08), 122.80, 123.64, 125.65 (125.67), 148.13, 148.22, 153.81 (154.50), 156.65 (156.16), 162.53, 175.20 (175.17) ppm; MS (CI): m/z 423.2 (MH⁺, 100). Anal. Calcd for C₂₅H₂₆O₆: C, 71.07; H, 6.20. Found: C, 71.33; H, 6.07.

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A compound having formula (I) or pharmaceutically acceptable salt thereof:

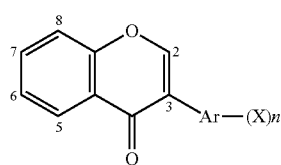

(I)

wherein Ar is phenyl; n is an integer from 1 to 5; each X is independently a halide, or alkoxy, or more than one X on Ar together form a cyclic ether structure; and wherein the compound is substituted on the C-2 position with H, alkyl, cycloalkyl or alkoxy, substituted on the C-5, C-6, and C-7 positions independently with H, hydroxy (OH), alkyl, cycloalkyl, alkoxy, acetyl, ester, acetoxy, substituted on the C-8 position with hydroxy (OH), cycloalkyl, alkoxy, acetyl, ester, acetoxy, CH₂OY¹ where Y¹ is hydrogen, alkyl, acetyl or the substituents on either C-6 and C-7 or the substituents on C-7 and C-8 together form a substituted or unsubstituted, saturated or unsaturated, cyclic or polycyclic ring structure which includes at least one chalcogen, wherein the alkyl, cycloalkyl, and alkoxy substituents can be substituted with one or more of a hydroxy, ester, acetoxy, alkoxy, or carbonyl.

2. The compound of claim 1, wherein the substituents on C-6 and C-7 or the substituents on C-7 and C-8 together form a substituted or unsubstituted, saturated or unsaturated, cyclic or polycyclic ring structure which includes at least one oxygen.

3. A compound having formula (I) or a pharmaceutically acceptable salt thereof:

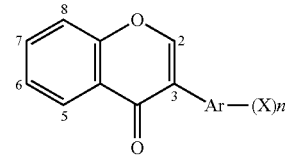

(I)

wherein Ar is diazinyl, pyrimidinyl, oxazolyl or imidazolyl; n is an integer from 1 to 5; each X is independently a halide, or alkoxy, or more than one X on Ar together form a cyclic ether structure; and wherein the compound is substituted on the C-2 position with H, alkyl, cycloalkyl or alkoxy, substituted on the C-5, C-6, C-7, and C-8 positions independently with H, hydroxy (OH), alkyl, cycloalkyl, alkoxy, acetyl, ester, acetoxy, or the substituents on either C-6 and C-7 or the substituents on C-7 and C-8 together form a substituted or unsubstituted, saturated or unsaturated, cyclic or polycyclic ring structure which includes at least one chalcogen.

4. The compound of claim 1 wherein the C-7 substituent is hydroxy (OH), alkyl, cycloalkyl, alkoxy, acetyl, ester, or acetoxy, and the C-8 substituent is alkoxy, acetyl, ester, acetoxy, or CH₂OY¹.

5. The compound of claim 1, wherein the C-2 substituent is hydrogen H or methyl; Ar includes one or two X groups on the aryl that can be halogens or alkoxy groups or together form a ring structure; the C-5 substituent is H, hydroxy or alkoxy; the C-6 substitutent is hydrogen H; the C-7 substituent is hydroxy or alkoxy; or either C-6 and C-7 together or C-7 and C-8 together form a ring structure including an oxygen.

6. A pharmaceutically acceptable composition comprising a compound of claim 1 or a pharmaceutically acceptable salt thereof and a pharmaceutically acceptable additive.

7. A method of treating prostate cancer, the method comprising administering to a patient in need of such treatment an effective amount of a compound of claim 1 or pharmaceutically acceptable salt thereof or a pharmaceutical composition thereof.

8. A pharmaceutically acceptable composition comprising a compound of claim 3 or a pharmaceutically acceptable salt thereof and a pharmaceutically acceptable additive.

9. The compound of claim 1, wherein the C-7 substituent is hydroxy (OH), alkoxy, acetyl, or acetoxy, and the C-8 substituent is CH₂OY¹.

10. The compound of claim 1, wherein the substituents on C-6 and C-7 together form a substituted or unsubstituted, saturated or unsaturated, cyclic or polycyclic ring structure which includes at least one oxygen.

11. The compound of claim 1, wherein the substituents on C-7 and C-8 together form a substituted or unsubstituted, saturated or unsaturated, cyclic or polycyclic ring structure which includes at least one oxygen.

12. The compound of claim 1, having one of the following formula or a pharmaceutically acceptable salt thereof:

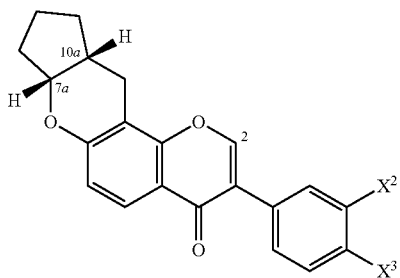
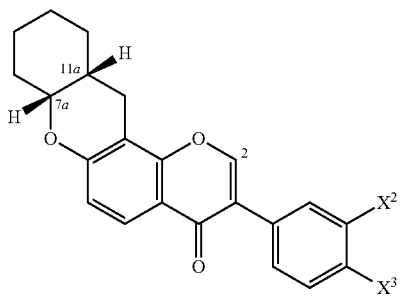
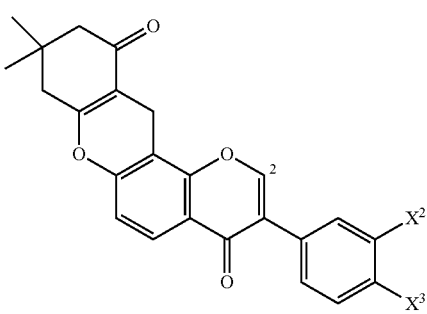
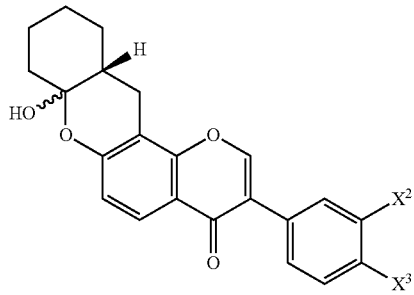
wherein each of $X^2$ and $X^3$ is independently a halide, or alkoxy, or $X^2$ and $X^3$ together form a cyclic ether structure.
13. A compound having one of the following formula or a pharmaceutically acceptable salt thereof:
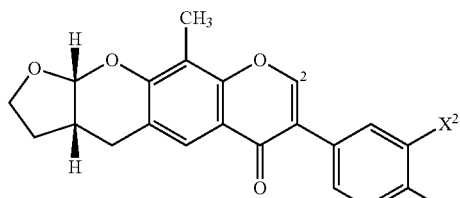
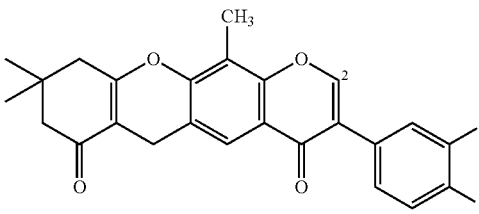
wherein each of $X^2$ and $X^3$ is independently a halide, or alkoxy, or $X^2$ and $X^3$ together form a cyclic ether structure.
* * * * *